(12) United States Patent
McClunan

(10) Patent No.: US 11,883,327 B2
(45) Date of Patent: Jan. 30, 2024

(54) SHUNT SYSTEM, SHUNT AND METHOD FOR TREATING AN OCULAR DISORDER

(71) Applicant: LIQID MEDICAL PROPRIETARY LIMITED, Cape Town (CA)

(72) Inventor: Daemon Bruce McClunan, Cape Town (CA)

(73) Assignee: LIQID MEDICAL PROPRIETARY LIMITED, Cape Town (ZA)

( * ) Notice: Subject to any disclaimer, the term of this patent is extended or adjusted under 35 U.S.C. 154(b) by 1258 days.

(21) Appl. No.: 16/344,251

(22) PCT Filed: Nov. 2, 2017

(86) PCT No.: PCT/IB2017/056817
§ 371 (c)(1),
(2) Date: Apr. 23, 2019

(87) PCT Pub. No.: WO2018/083620
PCT Pub. Date: May 11, 2018

(65) Prior Publication Data
US 2019/0247231 A1    Aug. 15, 2019

(30) Foreign Application Priority Data
Nov. 2, 2016    (ZA) .................................. 2016/07546

(51) Int. Cl.
*A61F 9/007*        (2006.01)
*A61B 17/02*        (2006.01)
(Continued)

(52) U.S. Cl.
CPC ...... *A61F 9/00781* (2013.01); *A61B 1/00154* (2013.01); *A61B 17/0231* (2013.01);
(Continued)

(58) Field of Classification Search
CPC .... A61F 9/007; A61F 9/00781; A61F 9/0017; A61F 9/00736; A61F 2/14;
(Continued)

(56) References Cited

U.S. PATENT DOCUMENTS 4,995,856 A * 2/1991 Heindl ................ A61M 27/006
604/9
5,171,213 A * 12/1992 Price, Jr. ............. A61F 9/00781
604/9
(Continued)

OTHER PUBLICATIONS

Liqid Medical Proprietary Limited; International Patent Application No. PCT/IB2017/056817; International Search Report: dated Feb. 15, 2018; (1 page).

*Primary Examiner* — Kai H Weng
(74) *Attorney, Agent, or Firm* — Dority & Manning, P.A.

(57) ABSTRACT

A shunt 10 for implantation in the human body for treating ocular disorders related to disorders of intraocular or intracranial pressure by providing for flow of aqueous fluid in the anterior chamber A of the eye and cerebrospinal fluid in the subarachnoid space B surrounding the optic nerve C. The shunt has a proximal end 12 which is implanted in the ocular anterior chamber and a distal end 14 which is implanted in the subarachnoid space. The shunt has a two-part construction, including a flexible distal tube 18 and a rigid proximal tube 20. The distal tube has a distal stop formation 26 near the distal end 14 which is located in the subarachnoid space (Continued)

upon implantation of the distal end, resisting withdrawal of the shunt. The proximal tube has a curved portion which conforms to the anatomical curvature of the ocular globe.

26 Claims, 24 Drawing Sheets

(51) Int. Cl.
 *A61B 1/00* (2006.01)
 *A61B 3/00* (2006.01)
 *A61F 9/00* (2006.01)

(52) U.S. Cl.
 CPC ........ *A61F 9/007* (2013.01); *A61B 3/00* (2013.01); *A61F 2009/0052* (2013.01); *A61M 2210/0612* (2013.01)

(58) Field of Classification Search
 CPC .... A61F 2009/00891; A61F 2250/0067; A61F 9/0008; A61M 2210/0612; A61M 27/002
 See application file for complete search history.

(56) References Cited

U.S. PATENT DOCUMENTS

| | | | |
|---|---|---|---|
| 5,300,020 A * | 4/1994 | L'Esperance, Jr. | ......................... A61F 9/00781 604/9 |
| 6,007,511 A * | 12/1999 | Prywes | ............... A61F 9/00781 604/9 |
| 7,431,709 B2 * | 10/2008 | Pinchuk | .............. A61F 9/00781 604/9 |
| 7,488,303 B1 * | 2/2009 | Haffner | ............... A61F 9/00781 604/521 |
| 9,017,276 B2 | 4/2015 | Horvath | |
| 9,168,172 B1 | 10/2015 | Berdahl | |
| 9,468,558 B2 | 10/2016 | Baerveldt | |
| 2007/0027470 A1* | 2/2007 | Dodick | ............... A61F 9/00736 606/213 |
| 2014/0236066 A1* | 8/2014 | Horvath | .................. A61L 31/08 604/9 |
| 2014/0243730 A1 | 8/2014 | Horvath | |
| 2015/0100010 A1 | 4/2015 | Baerveldt | |
| 2016/0067084 A1 | 3/2016 | Karageozian | |

* cited by examiner

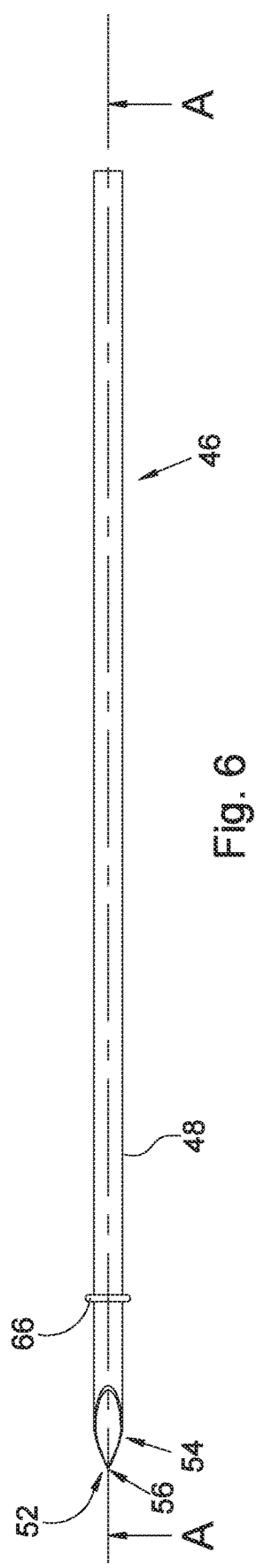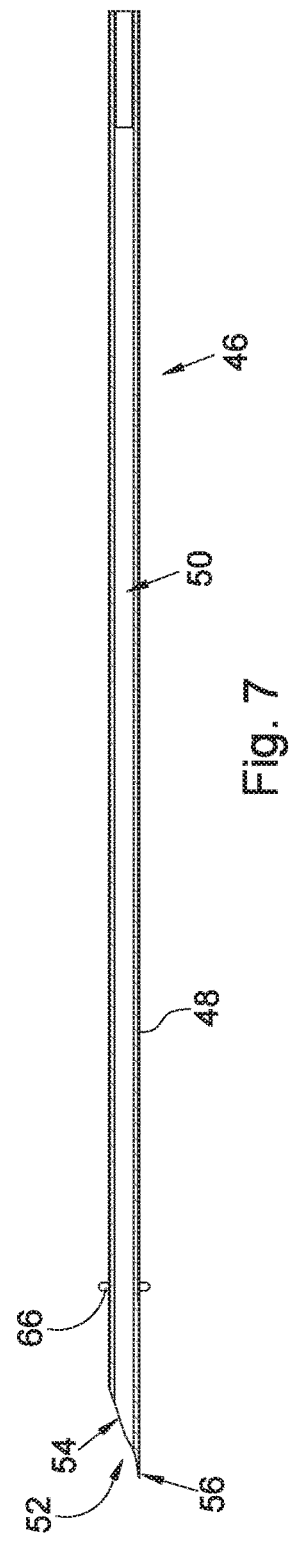

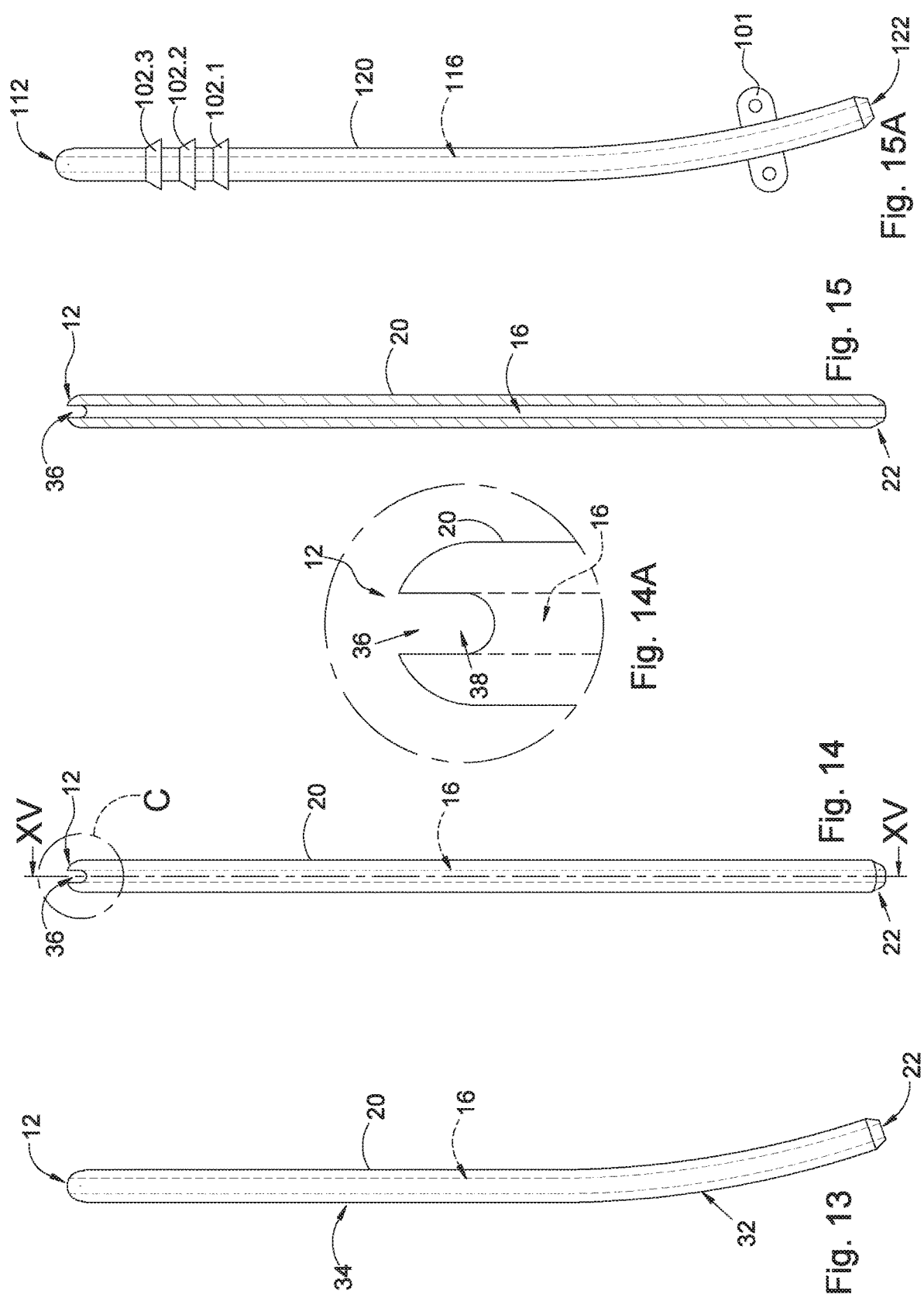

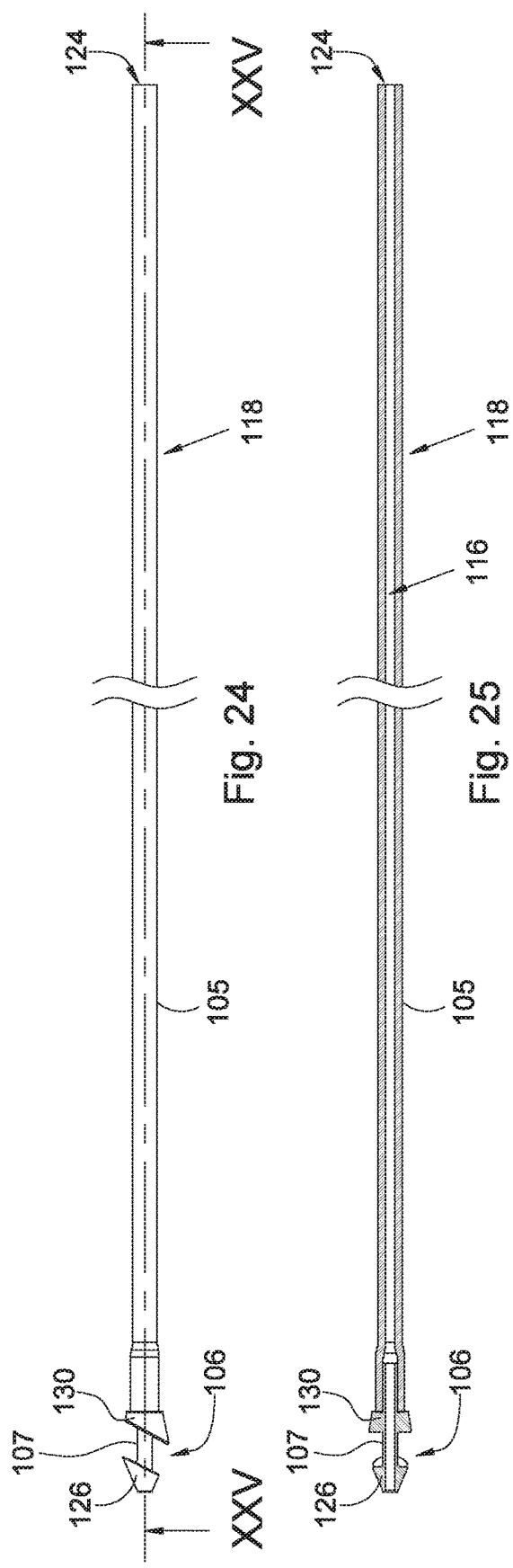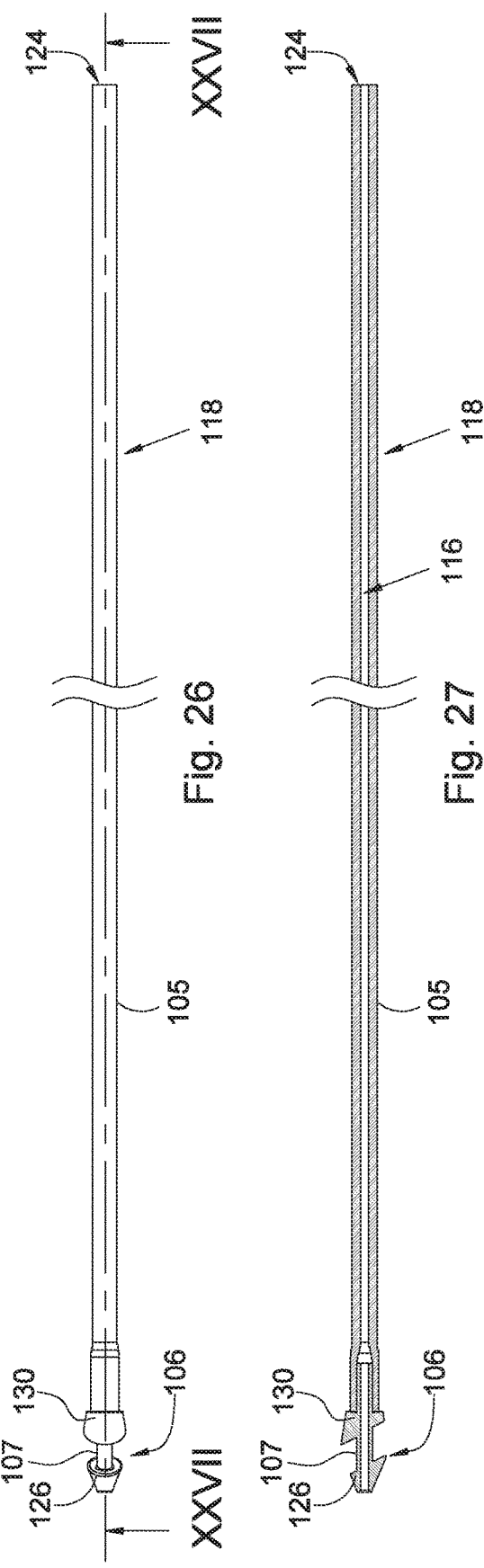

SHUNT SYSTEM, SHUNT AND METHOD FOR TREATING AN OCULAR DISORDER

This application is a National Stage Patent Application of PCT/IB2017/056817, filed on Nov. 2, 2017, which claims the benefit of priority to South African Patent Application No. 2016/07546, filed on Nov. 2, 2016, the disclosures of all of which are incorporated by reference herein in their entireties.

FIELD OF INVENTION

This invention relates to a shunt system for treating an ocular disorder related to an intraocular or intracranial disorder in a patient. The invention relates also to a method for treating an ocular disorder related to an ocular disorder of intraocular or intracranial pressure in a patient. More specifically, the invention relates to a shunt system and method for implanting a shunt between the eye and the subarachnoid space surrounding the optic nerve of a patient. The invention extends to the shunt of the shunt system.

BACKGROUND TO INVENTION

The implantation of a shunt connecting the anterior chamber of the ocular globe and the subarachnoid space is a procedure which, in order to be successful, needs to overcome the following difficulties: creating a clear passage from an external side of the optic nerve sheath to access the optic nerve sheath; penetrating the optic nerve sheath to access the subarachnoid space; ensuring a fluid-tight seal of the optic nerve sheath around the shunt; preventing damage to the optic nerve; preventing migration of the shunt; preventing shunt erosion through the conjunctiva; preventing blockage of the shunt by iris tissue and preventing corneal endothelial decompensation.

The subarachnoid space surrounding the optic nerve is formed between the optic nerve and the sheath and is filled with cerebrospinal fluid. Cerebrospinal fluid has a chemical composition comparable to that of the aqueous fluid of the eye. The pressure within cerebrospinal fluid normally varies between 5 mmHg and 15 mmHg.

The ocular globe of the eye has a tough outer layer comprised of the sclera and the cornea. The ocular globe maintains an internal pressure known as the intraocular pressure which normally varies between 10 mmHg and 21 mmHg. The intraocular pressure needs to be controlled within a defined range in order for the eye to function normally.

The intraocular pressure is regulated by maintaining a balance between volumes of aqueous fluid produced and drained from the anterior chamber of the ocular globe. Aqueous is produced by the ciliary body and drained through the trabecular and uveoscleral pathways. If an imbalance occurs in the amount of aqueous produced or drained from the ocular globe, then the intraocular pressure becomes too high or too low.

The lamina cribrosa separates the intraocular and subarachnoid fluid compartments. The presence of raised intraocular pressure or low intracranial pressure results in a large pressure differential across the lamina cribrosa (translaminar pressure). This causes damage to the optic nerve head known as glaucoma. Glaucoma causes irreversible visual field defects. These defects enlarge until a patient's field of view is severely restricted. In the end stage of the disease, total vision loss occurs. Glaucoma is a leading cause of blindness worldwide. If the intraocular pressure remains very high, the eye can become persistently painful and may need to be removed.

Current medical and surgical treatment options for glaucoma are aimed at lowering intraocular pressure. These treatments have various shortcomings. Glaucoma which is difficult to control is often managed by inserting a glaucoma drainage device. These devices drain the excess fluid out of the anterior chamber of the eye into one of 3 anatomical areas:

1) The subtenon's space

This space is not adapted to the presence of pressurised aqueous fluid. The aqueous therefore incites an inflammatory response which results in the formation of a fibrovascular "bleb". Consequently there is a high rate of complications, unpredictable outcomes and treatment failure.

2) The suprachoroidal space

This space is highly vascular and thus there is a high risk of bleeding. Outcomes are unpredictable and there is a high rate of failure.

3) The canal of schlemm

Only a small amount of fluid can drain through this space and thus the effect of these devices is minimal and treatment failure is common.

It is an object of the present invention to provide a method and a shunt system for draining excess fluid out of the ocular anterior chamber into the orbital subarachnoid space. This has the following advantages: Immediate, predictable, regulated and long-term pressure control, eradication of translaminar pressure, no bleb complications and less risk of intraocular bleeding.

Longstanding low intraocular pressure occurs when the ciliary body stops producing aqueous fluid. Phthisis is a disease caused by chronic low intraocular pressure wherein the ocular globe loses its integrity, stops functioning and shrivels up into a prune-like structure resulting in permanent and irreversible destruction of the eye. Phthisis is a leading indication for removal of an eye. Currently, no medical or surgical treatment options exist which can effectively reverse chronically low intraocular pressure.

The cerebrospinal fluid pressure is controlled by maintaining a balance between volumes of cerebrospinal fluid produced and drained from the subarachnoid space. Cerebrospinal fluid is produced by the choroid plexuses and drained through the arachnoid granulations. If more cerebrospinal fluid is produced than is drained from the subarachnoid space, then the cerebrospinal fluid pressure becomes too high. This can cause damage to the optic nerve head due to reversed translaminar pressure. Idiopathic Intracranial Hypertension is a condition where longstanding raised intracranial pressure causes loss of vision.

It is a further object of the present invention to provide a method and shunt system for connecting the ocular globe and subarachnoid space to allow cerebrospinal fluid to flow into the ocular globe until the intraocular pressure is equal to the intracranial pressure, thereby preventing the onset of phthisis and Idiopathic Intracranial Hypertension.

In a specific application, the present invention provides for the implantation of a shunt for the regulation of intraocular pressure in order to ameliorate the abovementioned ocular diseases.

SUMMARY OF INVENTION

According to a first aspect of the invention there is provided a shunt for treating an ocular disorder related to a disorder of intraocular or intracranial pressure in a patient, the shunt having a proximal end which is implantable in an ocular anterior chamber of a patient and a distal end which is implantable in a subarachnoid space of the patient, the shunt defining a lumen extending longitudinally between the distal and proximal ends, the shunt having an enlarged distal stop formation which is disposed in the subarachnoid space after implantation of the distal end region of the shunt in the subarachnoid space, for resisting withdrawal of the shunt after implantation in the subarachnoid space, and being flexible along a portion of a length of the shunt so as to conform to an anatomical curvature of the ocular globe.

The shunt may have an enlarged proximal stop formation near the distal end of the shunt disposed at a position spaced from the distal stop formation at a location relatively closer to the proximal end of the shunt, the proximal stop formation being disposed externally of the optic nerve sheath upon implantation of the distal end of the shunt in the subarachnoid space, thereby preventing over-migration of the shunt into the subarachnoid space.

The shunt may comprise a distal shunt portion defining the distal end of the shunt and a proximal shunt portion defining the proximal end of the shunt.

The distal shunt portion may be of a flexible construction along a portion of a length thereof and wherein the proximal shunt portion is of a rigid construction facilitating advancement of the proximal shunt portion along a scleral passageway defined in the sclera extending to the ocular anterior chamber.

The distal shunt portion may be flexible along an entire length thereof.

The distal shunt portion may comprise an elongate flexible tubular body and a rigid implant body connected to a distal end of the flexible tubular body, which defines the distal end of the shunt.

The distal end of the shunt may have a tapered end region tapering towards the distal end of the shunt, for facilitating advancement of the distal end region of the shunt along a passageway defined in the optic nerve sheath.

The implant body may define the distal stop formation and the proximal stop formation.

A cross-sectional width of the proximal stop formation may be less than a cross-sectional width of the distal stop formation.

The proximal shunt portion may have a straight section at a proximal end region of the shunt terminating in the proximal end of the shunt, permitting the straight section to be displaced along a scleral passageway defined in the sclera extending to the ocular anterior chamber.

A proximal end region of the proximal shunt portion may taper towards the proximal end of the shunt, thereby facilitating displacement of the proximal shunt portion along the scleral passageway.

A wall of the proximal shunt portion may have an opening at the proximal end thereof and at least one opening in a side thereof thereby permitting drainage of aqueous fluid into the lumen of the shunt from different directions.

The proximal shunt portion may have a curved section spaced from the proximal end of the shunt, the curved section having a curvature which conforms to an anatomical curvature of the ocular globe.

The proximal shunt portion may include at least one outwardly-projecting ridge formation for resisting migration of the proximal shunt portion after implantation thereof in the ocular anterior chamber.

The proximal shunt portion may include a number of the ridge formations in a longitudinally-spaced arrangement near the proximal end of the shunt.

The proximal shunt portion may include an outwardly-projecting locating formation for engagement by a suture for suturing the proximal shunt portion to the sclera to hold the proximal shunt portion in place.

The distal shunt portion may comprise a flexible distal tube and wherein the proximal shunt portion comprises a rigid proximal tube, the distal tube and the proximal tube being releasably connected to one another with the lumen of the shunt extending continuously through the distal and proximal tubes.

A spacing between the distal stop formation and the proximal stop formation may be such that opposing sides of the distal stop formation and the proximal stop formation define abutment faces which abut opposite sides of the optic nerve sheath thereby providing for secure location of the shunt relative to the optic nerve sheath.

The shunt may define a fluid flow opening leading into the lumen at the distal end of the shunt.

The distal stop formation may be deformable. More specifically, the distal stop formation may be resiliently compressible.

A distal end of the shunt may be closed, with one or more fluid flow openings leading into the lumen being defined in a side wall of the shunt near the distal end thereof.

The shunt may incorporate an elutable therapeutic substance. More specifically, the elutable therapeutic substance may be selected from a group consisting of an antibiotic, an anticlotting agent, and an anti-vascular endothelial growth factor.

According to a second aspect of the invention there is provided a shunt system for treating an ocular disorder related to a disorder of intraocular or intracranial pressure in a patient, the shunt system including:
 a shunt having an elongate tubular configuration, the shunt having a proximal end which is implantable in the ocular anterior chamber of a patient and a distal end which is implantable in the subarachnoid space of the patient, the shunt defining a lumen extending longitudinally between the distal and proximal ends, the shunt having an enlarged stop formation near the distal end thereof for resisting withdrawal of the shunt after implantation; and
 a shunt inserting device including:
  a) a distal insertion portion for displaceably supporting the shunt, the distal insertion portion defining a tissue-penetrating tip for penetrating the optic nerve sheath so as to form a passage in the optic nerve sheath; and
  b) a shunt advancing device for displacing the shunt through the passage in the optic nerve sheath for implanting the distal end of the shunt in the subarachnoid space.

The distal insertion portion of the shunt inserting device may comprise an elongate hollow shaft defining an internal passageway within which the shunt is slidably received and displaceable.

The distal end of the shunt may be closed, the shunt advancing device including an elongate advancing element having a proximal end and a distal end, the distal end of the advancing element being located slidably within the hollow shaft for abutment with an inner side of the closed distal end of the shunt for exerting a force on the distal end of the shunt for advancing the shunt, the shunt defining at least one fluid flow opening near the distal end extending into the lumen of the shunt for permitting fluid to pass therethrough.

The shunt inserting device may include a housing to which the distal inserting portion is mounted, the shunt advancing device including a hand-operated slider which is slidably mounted to the housing, the slider including an actuator which is engaged with the advancing element for advancing the advancing element and thereby the shunt within the hollow shaft.

The hollow shaft of the distal insertion portion may comprise a lancet having a taper cut at the distal end thereof defining a discharge opening through which the shunt is advanced.

The taper cut may have a distal end and a proximal end and wherein a distal end region of the taper cut defining the tissue-penetrating tip of the lancet, is sharp-edged while a proximal end region of the taper cut has blunt edges.

The taper cut may be defined by a first bevel cut proximate the proximal end of the taper cut and a second bevel cut proximate the distal end of the taper cut, the sharp-edged distal end region of the taper cut comprising a portion of the second bevel cut and the blunt-edged proximal end region comprising the first bevel cut and a remaining portion of the second bevel cut adjacent the sharp-edged distal end region.

The shunt may have a flexible distal end region and a resiliently compressible, enlarged distal stop formation near the distal end thereof, the distal stop formation being locatable with the subarachnoid space upon implantation of the distal end therein and compressible when received within the internal passageway of the hollow shaft of the distal insertion portion of the shunt inserting device and expandable after passing through the discharge opening of the distal insertion portion, thereby preventing withdrawal of the distal end of the tubular member from the subarachnoid after implantation of the shunt within the subarachnoid space.

The hollow shaft may have an outwardly-projecting stop formation spaced from the tissue-penetrating tip for preventing over-insertion of the hollow shaft into the subarachnoid space.

The distal insertion portion may comprise an inner lancet defining the tissue-penetrating tip and a tubular outer support member which is co-axially disposed relative to the lancet and spaced therefrom so as to define an annular space between the lancet and the outer support member within which the shunt is slidably received and displaceable.

The lancet may have a taper cut at the distal end.

The taper cut may have a distal end and a proximal end and wherein a distal end region of the taper cut defining the tissue-penetrating tip of the lancet, is sharp-edged while a proximal end region of the taper cut has blunt edges.

The taper cut may be defined by a first bevel cut proximate the proximal end of the taper cut and a second bevel cut proximate the distal end of the taper cut, the sharp-edged distal end region of the taper cut comprising a portion of the second bevel cut and the blunt-edged proximal end region comprising the first bevel cut and a remaining portion of the second bevel cut adjacent the sharp-edged distal end region.

According to a third aspect of the invention there is provided a method for treating an ocular disorder related to a disorder of intraocular or intracranial pressure in a patient, the method including:

providing a shunt comprising an elongate tubular body having a distal end and a proximal end and defining a lumen extending longitudinally between the distal and proximal ends;

providing a shunt inserting device having a distal insertion portion in which the shunt is displaceably supported, the distal insertion portion defining a tissue-penetrating tip;

creating a passageway through orbital connective tissues surrounding the ocular orbit and the optic nerve sheath;

inserting the shunt inserting device into the passageway;

inserting the tissue-penetrating tip of the distal insertion portion of the shunt inserting device into the subarachnoid space surrounding the optic nerve so as to form a passage through the optic nerve sheath leading into the subarachnoid space;

the shunt inserting device advancing the distal end of the shunt distally into the subarachnoid space;

withdrawing the shunt inserting device from the ocular orbit; and inserting the proximal end of the shunt into the ocular anterior chamber, providing for fluid flow along the shunt between aqueous fluid in the ocular anterior chamber and cerebrospinal fluid in the subarachnoid space.

The method may include creating said passageway through the tenon's capsule and along the subtenon's space to reach the optic nerve sheath;

Insertion of the proximal end of the shunt device into the ocular anterior chamber may include penetrating the sclera of the eye so as to define a channel in the sclera and advancing the proximal end of the shunt through the channel into the ocular anterior chamber.

The method may include forming a passage in the sclera proximate the limbus to a position at an insertion point into the ocular anterior chamber around the trabecular meshwork using a surgical cutting instrument.

The method may include passing the tissue-penetrating tip of the shunt inserting device through the superonasal portion of the optic nerve sheath.

BRIEF DESCRIPTION OF THE DRAWINGS

Further features of the invention are described hereinafter by way of a non-limiting example of the invention with reference to and as illustrated in the accompanying diagrammatic drawings. In the drawings:

FIG. 6 shows a top view of the distal insertion tube of the shunt inserting device of FIG. 4;

FIG. 7 shows a sectional side view of the distal insertion tube of FIG. 6;

FIG. 13 shows a side view of the proximal tube of the shunt of FIG. 2A;

FIG. 14 shows another side of the proximal tube of the shunt of FIG. 2A;

FIG. 14A shows enlarged detail C of the proximal tube of FIG. 14;

FIG. 15 shows a sectional side view of the proximal tube of the shunt of FIG. 2A, sectioned along section line XV-XV of FIG. 14;

FIG. 15A shows a side view of another embodiment of the proximal tube of the shunt in accordance with the invention;

FIG. 24 shows a side view of the distal tube of FIG. 22;

FIG. 25 shows a sectional side view of the distal tube of FIG. 22, sectioned along section line XXV-XXV of FIG. 24;

FIG. 26 shows another side view of the distal tube of FIG. 22;

FIG. 27 shows a sectional side view of the distal tube of FIG. 22, sectioned along section line XXVII-XXVII of FIG. 26.

DETAILED DESCRIPTION OF THE INVENTION

Figure 1:
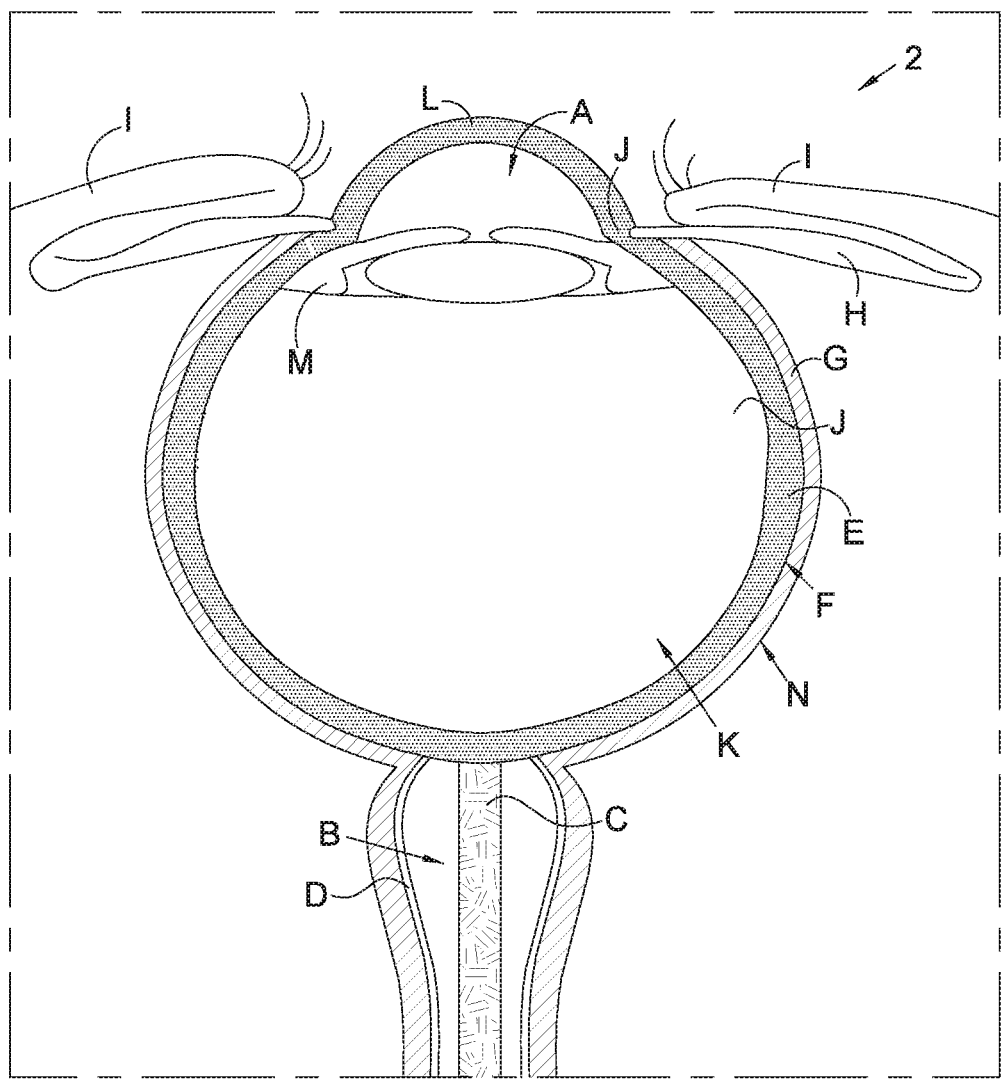
FIG. 1 shows a cross-sectional view of a human eye.

With reference to FIG. 1 of the drawings, a cross-sectional view illustrating anatomical parts of a human eye 2 which are required for use in the description which follows below, comprises:

A: Anterior chamber filled with aqueous fluid
B: Subarachnoid space filled with cerebrospinal fluid
C: Optic nerve
D: Optic nerve sheath
E: Sclera
F: Subtenon's space
G: Tenon's capsule
H: Conjunctiva
I: Eyelids
J: Limbus and trabecular meshwork
K: Posterior segment filled with vitreous jelly
L: Cornea
M: Ciliary body
N: Ocular globe With reference to FIGS. 1 to 20 of the drawings, a shunt in accordance with the invention, is designated generally by the reference numeral 10. The shunt 10 is adapted for implantation in the human body so as to provide for flow communication between aqueous fluid in the anterior chamber A of the eye and cerebrospinal fluid in the subarachnoid space B surrounding the optic nerve C. The shunt is adapted for treating ocular disorders related to disorders of intraocular or intracranial pressure in a patient. The shunt 10 when implanted, regulates intraocular pressure in the eye of a human patient. For the treatment of glaucoma, the shunt permits aqueous fluid to drain from the anterior chamber of the eye into the subarachnoid space, thereby reducing intraocular pressure. For the treatment of phthisis and idiopathic intracranial hypertension, the shunt permits the flow of cerebrospinal fluid which has a similar composition to aqueous fluid, to flow to the anterior chamber of the eye thereby increasing intraocular pressure.

The shunt 10 has an elongate tubular configuration having a proximal end 12 and a distal end 14. The shunt defines a lumen 16 which extends between the distal and proximal ends.

The shunt 10 is of a two-part construction, including a distal shunt portion comprising a flexible distal tube 18 of silicone rubber; and a proximal shunt portion comprising a rigid plastics proximal tube 20 of polyetheretherketone (PEEK). The rigid proximal tube 20 is removably connected to the flexible distal tube 18. This allows the surgeon to assess the function of the shunt and flush the lumen or inject a therapeutic substance through the shunt as required peri- or post-operatively. The distal tube 18 defines the distal end 14, while the proximal tube 20 defines the proximal end 12. Opposite ends 22, 24 of the proximal tube 20 and the distal tube 18, respectively, are removably connected. More specifically, the end 22 of the proximal tube 20 is press-fitted into the end 24 of the distal tube 18 in an arrangement wherein internal passages of the distal and proximal tubes form a continuous internal passage defining the lumen 16.

The rigidity of the proximal shunt portion facilitates its displacement along a narrow scleral passage which prevents aqueous fluid leakage and prevents tube erosion through conjunctival tissue.

The distal tube 18 has an enlarged resiliently compressible distal stop formation 26 in the form of an annular flange near the distal end 14. The distal stop formation 26 is spaced a predetermined distance from the distal end 14. The distal end 14 of the distal tube 18 is closed, with two fluid flow openings 28.1, 28.2 being defined on opposite sides of the distal tube at locations between the distal stop formation 26 and the distal end 14.

The shunt further includes an enlarged proximal stop formation 30 in the form of an annular flange which is spaced from the distal stop formation a predetermined distance at a position relatively closer to the proximal end of the distal tube.

The distal stop formation 26 resists withdrawal of the shunt after implantation of the shunt in the subarachnoid space, while the proximal stop formation 30 is disposed externally of the optic nerve sheath upon implantation of the distal end of the shunt in the subarachnoid space for preventing over-migration of the shunt into the subarachnoid space.

Figure 2:
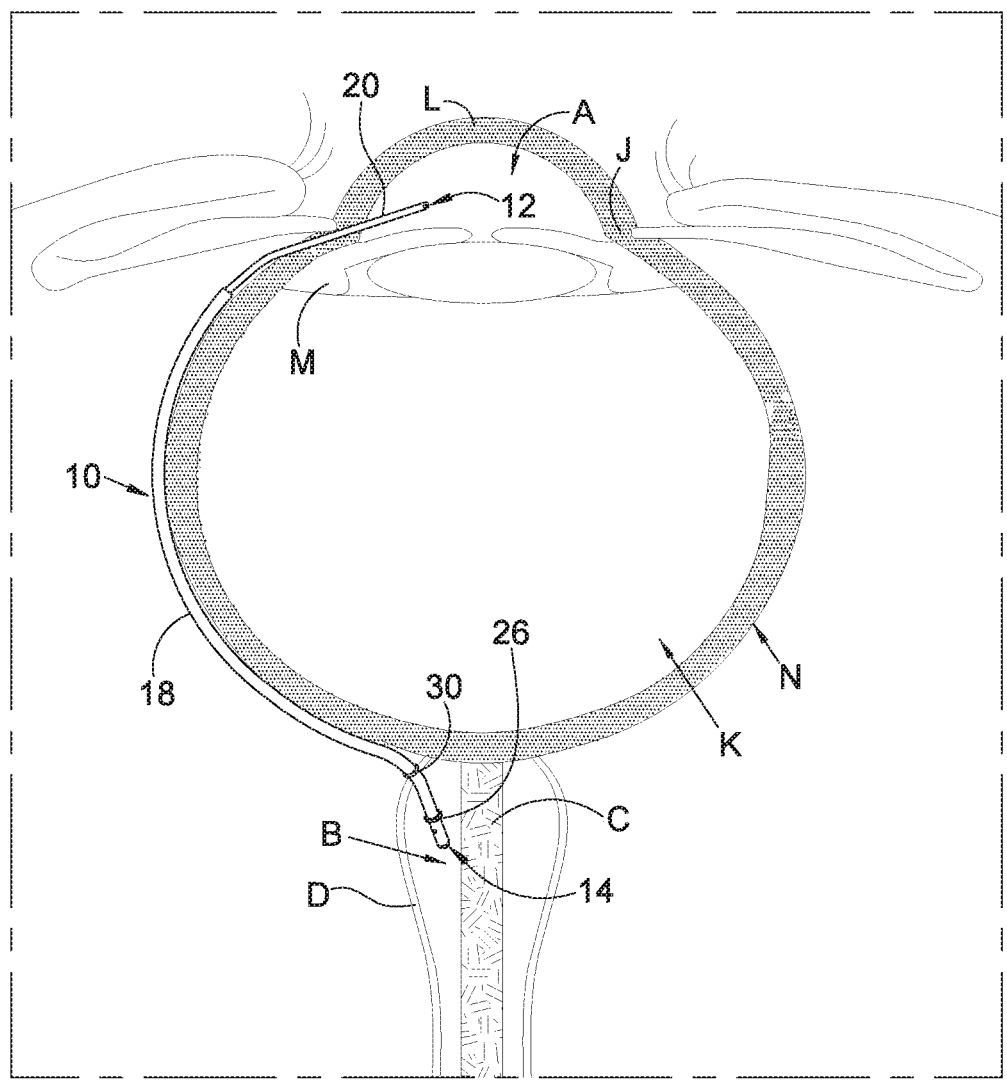
FIG. 2 shows a cross-sectional view of a human eye in which a first embodiment of a shunt in accordance with the invention, has been implanted to provide for fluid flow between the anterior chamber of a human eye and the subarachnoid space surrounding the optic nerve.
Figure 2A:
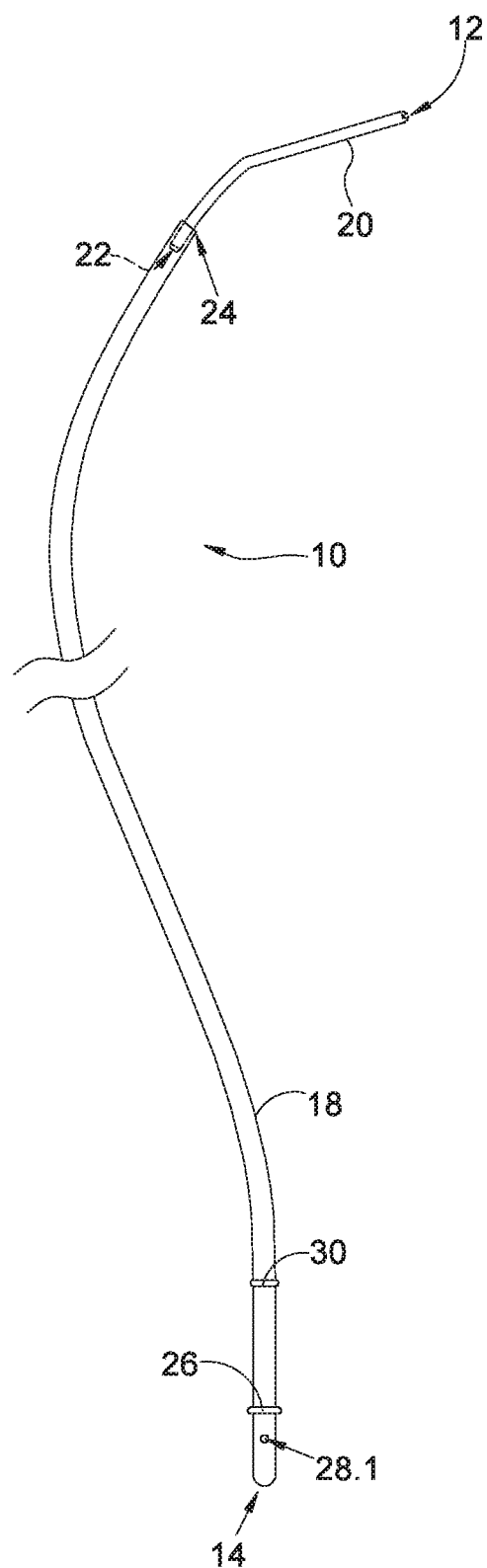
FIG. 2A shows a side view of the shunt of FIG. 2.
Figure 3A:
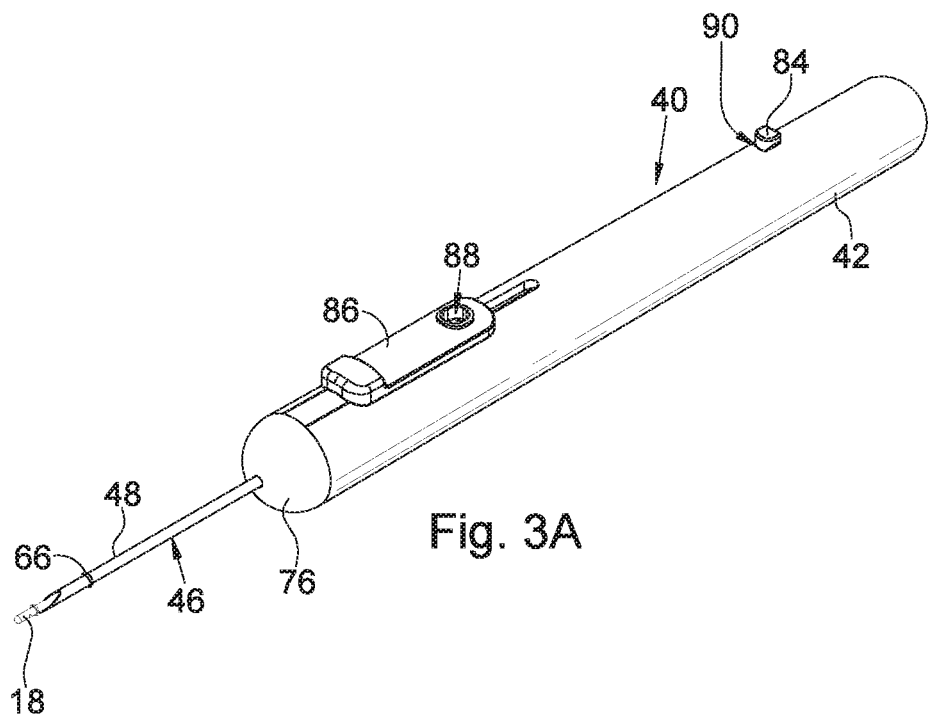
FIG. 3A shows a three-dimensional view of a shunt inserting device of a shunt system in accordance with the invention.
Figure 3B:
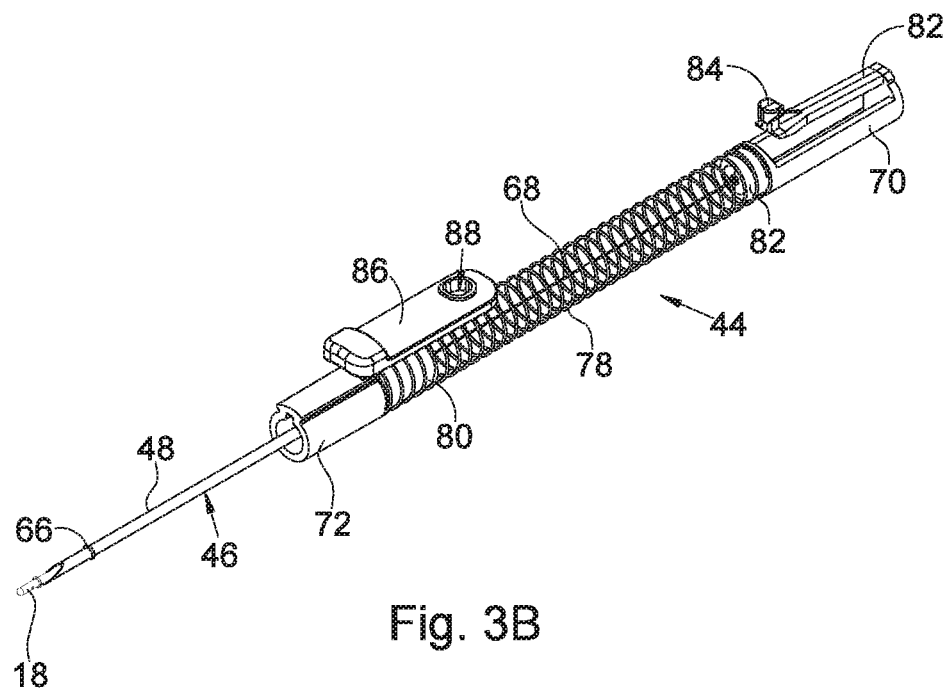
FIG. 3B shows a three-dimensional view of the shunt inserting device of FIG. 3A with the housing removed to show internal components thereof.
Figure 4:
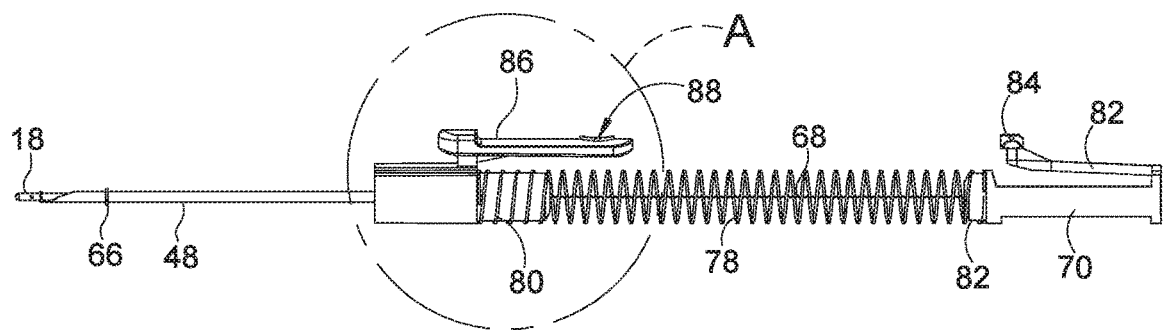
FIG. 4 shows a side view of the shunt inserting device of FIG. 3B.
Figure 5:
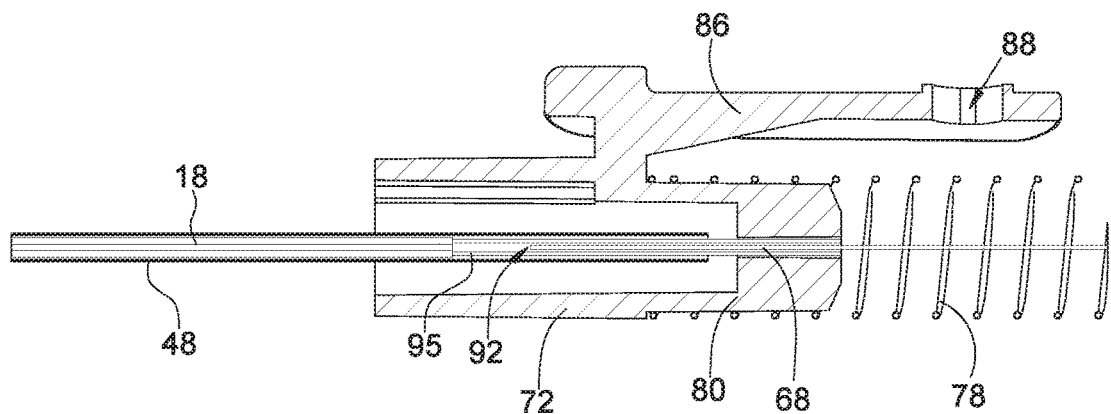
FIG. 5 shows enlarged detail A of the shunt inserting device of FIG. 4.

The proximal end 12 of the shunt is convexly rounded so as to provide the proximal tube with a tapered end facilitating displacement of the proximal tube along the scleral passageway towards the anterior chamber. The proximal tube 20 has a curved section 32 near the end 22 and a straight section 34 extending between the curved section and the proximal end 12. The curvature of the curved section conforms to the anatomical curvature of the ocular globe N as is shown in FIG. 2, thereby preventing erosion of the surrounding tissue. The straight section 34 is displaced along the scleral passageway from about 4 mm away from the corneal limbus to enter the anterior chamber at the trabecular meshwork.

The distal tube is approximately 30 mm in length and has an outer diameter of 1 mm or less. The flexibility of the distal tube allows the distal tube to conform to the anatomical curvature of the ocular globe with minimal resistance. The distal tube may incorporate an elutable therapeutic substance comprising one or more of an antibiotic, an anticlotting agent and an anti-vascular endothelial growth factor.

The proximal tube is approximately 10 mm in length and has an outer diameter of 0.5 mm or less. The relatively small outer diameter of the proximal tube prevents endothelial decompensation and tube erosion. The proximal tube defines a fluid flow opening 36 at the proximal end 12. The opening 36 is defined by a central opening at the proximal end 12 and a pair of opposed slots 38 defined in opposite sides of a wall of the proximal tube at the proximal end 12. These allow fluid to drain into the proximal end opening from multiple axes and prevent tube blockage by iris tissue.

With reference to FIG. 15A, another embodiment of a proximal tube of the shunt is designated by the reference numeral 120. The proximal tube is similar to the proximal tube 20 and, as such, the same and/or similar reference numerals are used in FIG. 15A to designate features of the proximal tube which are the same and/or similar to features of the proximal tube 20. A first difference is that the proximal tube 120 includes three spaced annular ridges 102.1, 102.2 and 102.3 near the proximal end 122 of the proximal tube to resist migration of the proximal tube after implantation in the ocular anterior chamber. A second difference is that the proximal tube 120 includes a fenestrated flare 101 providing for suturing of the proximal tube 120 to the sclera to hold the proximal tube in place.

The invention extends to a shunt system including the shunt 10 and a shunt inserting device 40 for implanting the shunt in the subarachnoid space surrounding the optic nerve. The shunt inserting device 40 comprises a tubular housing 42, a shunt advancing device 44 and a distal inserting portion 46 mounted to the housing. The housing 42 provides a handle by which the shunt inserting device can be held.

The distal insertion portion 46 comprises a lancet 48 defining an internal passageway 50 within which the distal tube 18 of the shunt is slidably located. The lancet has a distal end 52 defining a discharge opening 54 through which the distal tube is advanced. The distal end 52 defines a tissue-penetrating tip 56 for penetrating the optic nerve sheath.

Figures 8A, 8B:
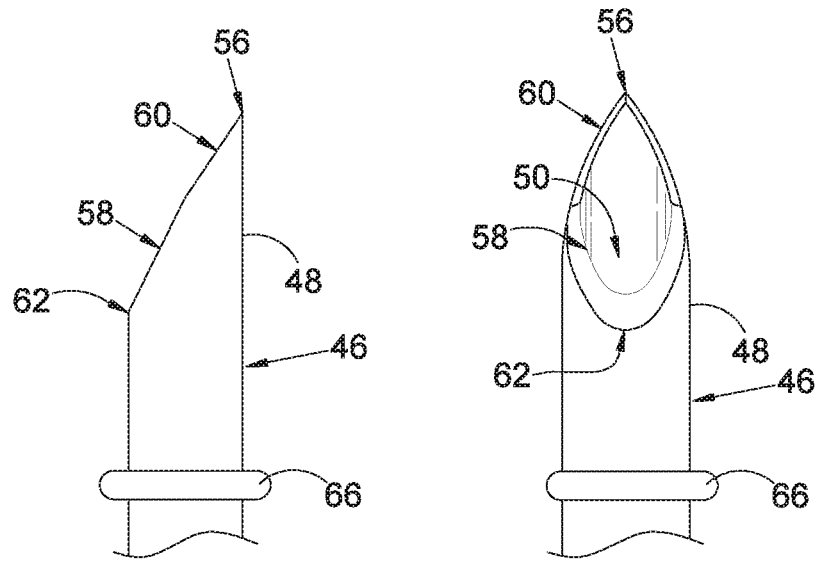
FIGS. 8A-8C show various views of the tissue-penetrating tip of the distal inserting tube of the shunt inserting device of FIG. 4, illustrating the manner in which the tissue penetrating tip is formed.
Figure 8C:
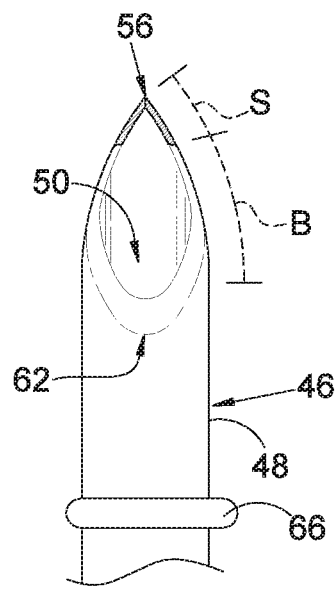
Figure 9:
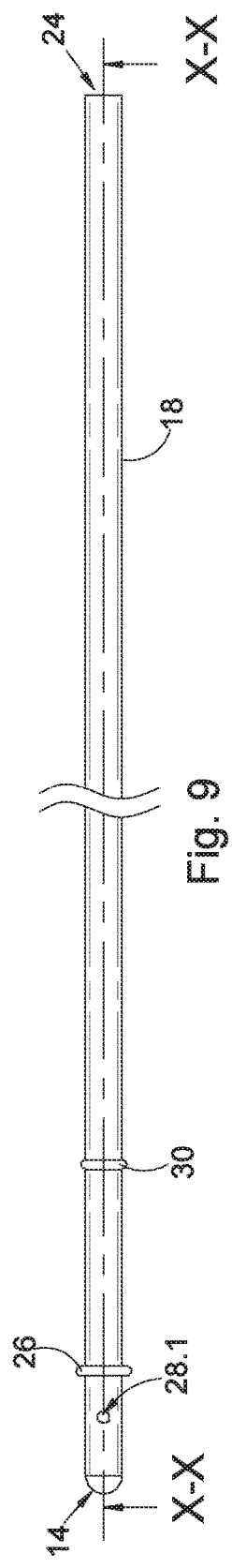
FIG. 9 shows a side view of the distal tube of the shunt of FIG. 2A.
Figure 10:
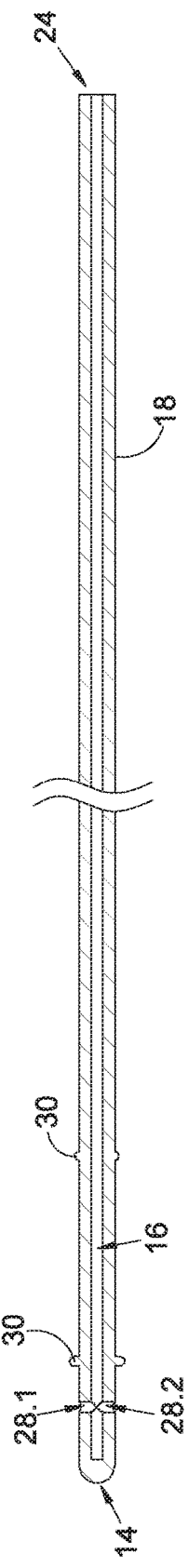
FIG. 10 shows a sectional side view of the distal tube of the shunt of FIG. 2A, sectioned along section line X-X of FIG. 9.
Figure 11:
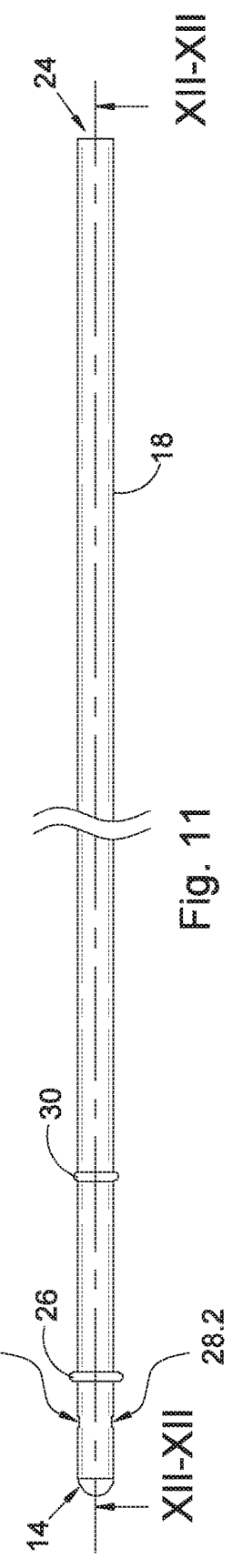
FIG. 11 shows another side view of the distal tube of the shunt of FIG. 2A.
Figure 12:
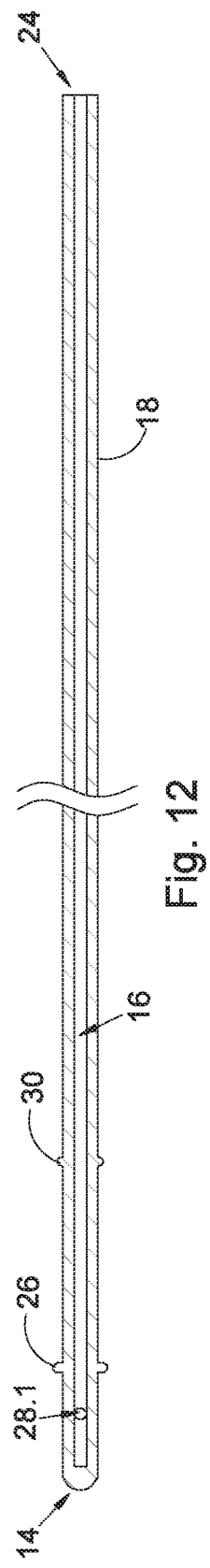
FIG. 12 shows a sectional side view of the distal tube of the shunt of FIG. 2A, sectioned along section line XII-XII of FIG. 11.

The distal end of the lancet is defined by a taper cut. With reference to FIGS. 8A-8C of the drawings, in order to form the taper cut, a first bevel cut 58 and a second bevel cut 60 is made at the distal end (see FIGS. 8A and 8B). The taper cut has a distal end coinciding with the tissue-penetrating tip 56 and a proximal end 62. The taper cut is defined by the first bevel cut 58 proximate the proximal end 62 and the second bevel cut 60 proximate the tissue-penetrating tip. The bevel cuts define sharp edges. After making the bevel cuts, the first bevel cut 58 and a portion of the second bevel cut 60 spaced from the tissue-penetrating tip, are blunted by rounding off sharp edges (see FIG. 8C) so as to prevent further cutting of tissue and promote maximal stretching, but not tearing, of tissue around the lancet as it is inserted into the optic nerve sheath in order to maximise a seal formed around the lancet by the optic nerve sheath, but also minimise inflammation. The tissue-penetrating tip and a portion of the second bevel cut adjacent the tissue-penetrating tip are not blunted and thus retain their sharp edged properties for cutting through the optic nerve sheath. The blunted regions of the first bevel cut and of a portion of the second bevel cut are designated by the reference letter "B" while the distal end region of the second bevel cut having sharp edges are designated by the reference letter "S" in FIG. 8C.

The lancet 48 has an enlarged stop formation 66 in the form of an annular flange at a location spaced a predetermined distance from the tissue-penetrating tip 56. The stop formation 66 is configured and dimensioned so as to abut against an external side of the optic nerve sheath thereby preventing over-insertion of the tissue-penetrating tip into the subarachnoid space.

The shunt advancing device 44 is configured for advancing the distal tube 18 of the shunt distally along the lancet 48 for inserting the distal end of the shunt into the subarachnoid space. The mechanism 44 includes an elongate advancing stylet 68.

The distal tube 18 is received within the internal passageway 50 of the lancet 48 and the stylet 68 is received within the lumen 16 of the distal tube. The mechanism 44 includes a piston 70 which is slidably displaceable along an internal passageway within the housing 42. The mechanism includes a slider block 72 at a distal end of the housing which is slidably supported within the housing and a mounting block 76 at the distal end which is fixedly mounted to the housing. The lancet 48 is fixedly mounted to the mounting block 76. A proximal end of the stylet is connected to the piston, while the slider block defines a passage within which the stylet is slidably located. A sleeve 95 is located within the mounting block for supporting the distal tube at its end 24.

The mechanism also include a coil spring 78 which is mounted at opposite ends thereof to spigot mounting formations 80, 82 of the slider block 72 and the piston 70, respectively. The coil spring is compressed when the piston is displaced towards the slider block resulting in the spring exerting a force on the piston 70 for urging the piston away from the slider block.

The piston has a resiliently deformable lever arm 82 having an engagement projection 84 at an end thereof, while the slider block 72 has a slider arm 86 defining a complementary engagement aperture 86 within which the projection 84 of the piston is receivable for releasably locking the piston to the slider block.

The housing 42 defines an aperture 90 at a proximal end region thereof within which the engagement projection of the piston 70 is received for releasably locking the piston to the housing in a retracted condition of the piston.

Figure 16A:
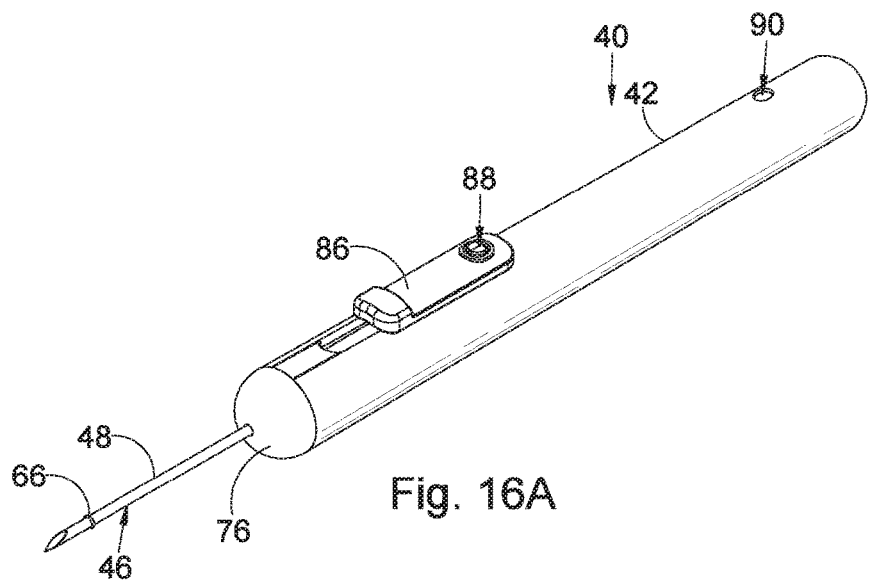
FIGS. 16A-16C show the shunt inserting device in a first mode of operation.
Figure 16B:
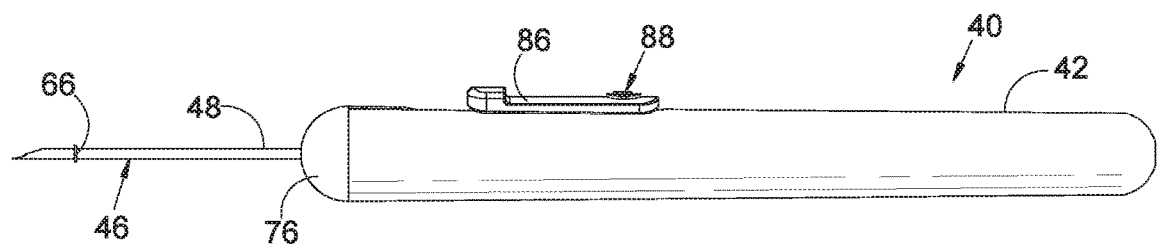
Figure 16C:
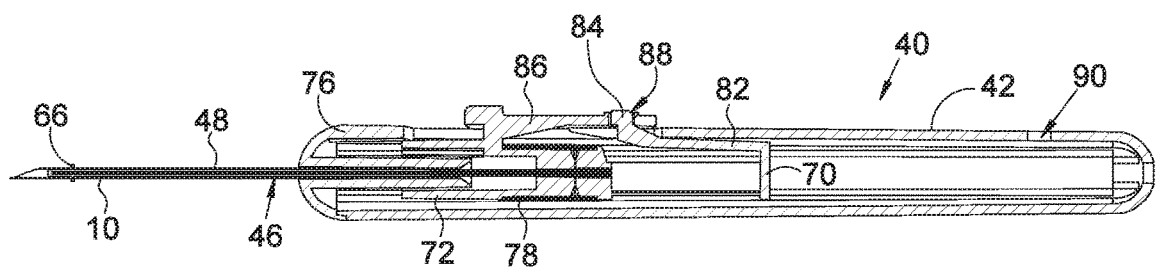
Figure 17A:
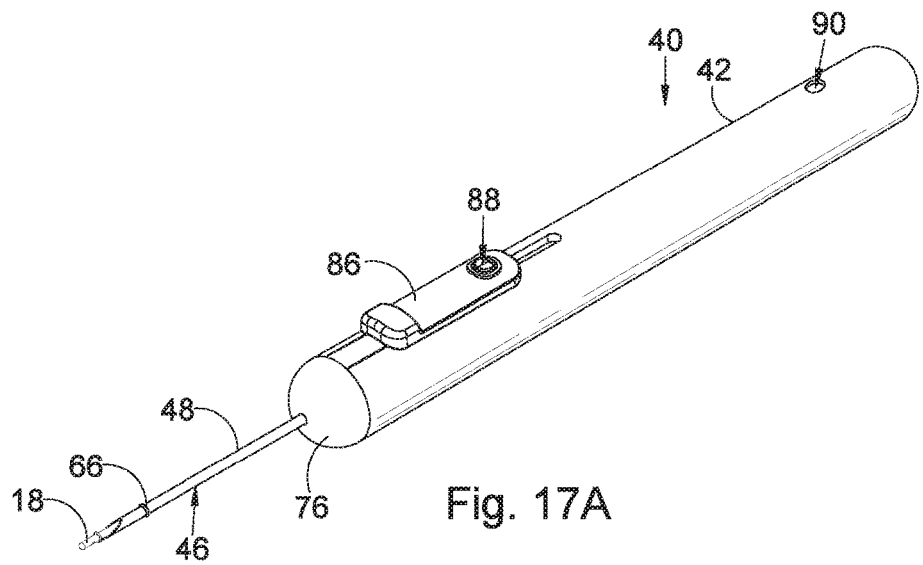
FIGS. 17A-17C show the shunt inserting device in a second mode of operation.
Figure 17B:
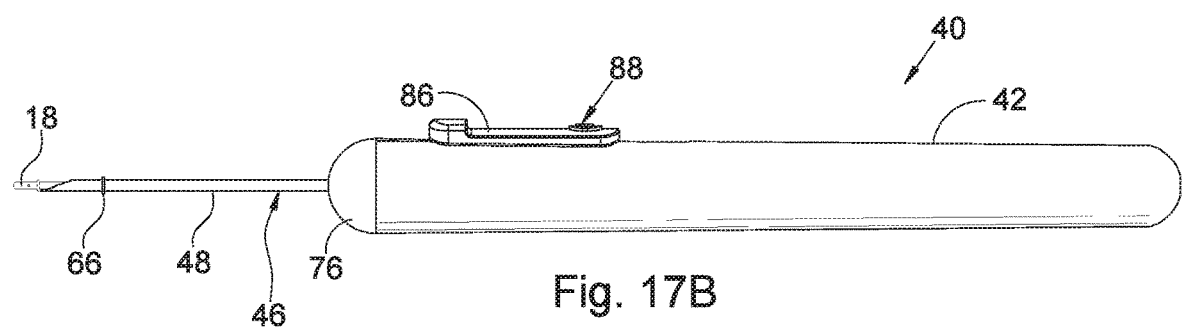
Figure 17C:
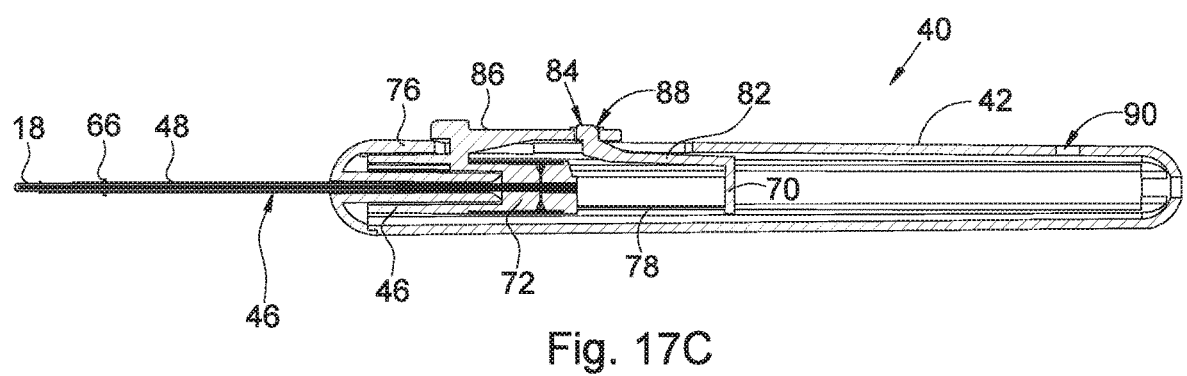
Figure 18A:
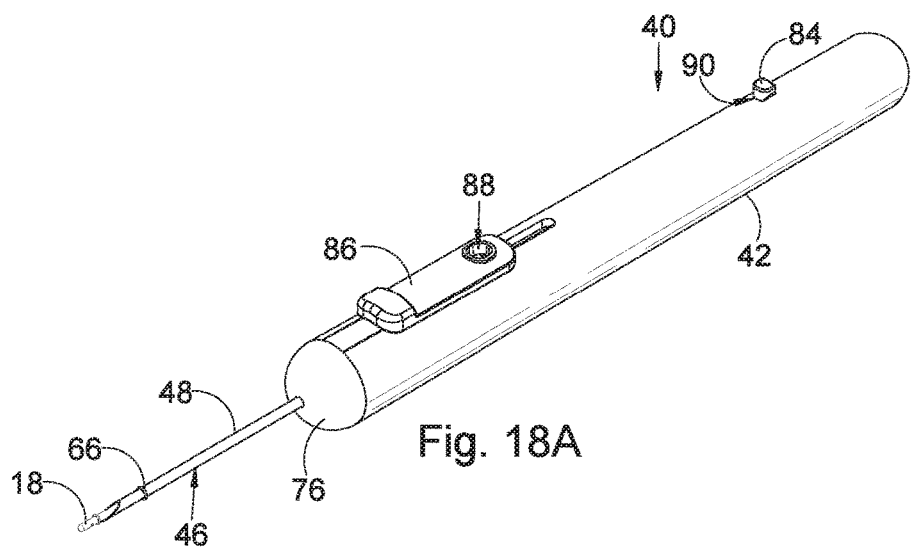
FIGS. 18A-18C show the shunt inserting device in a third mode of operation.
Figure 18B:
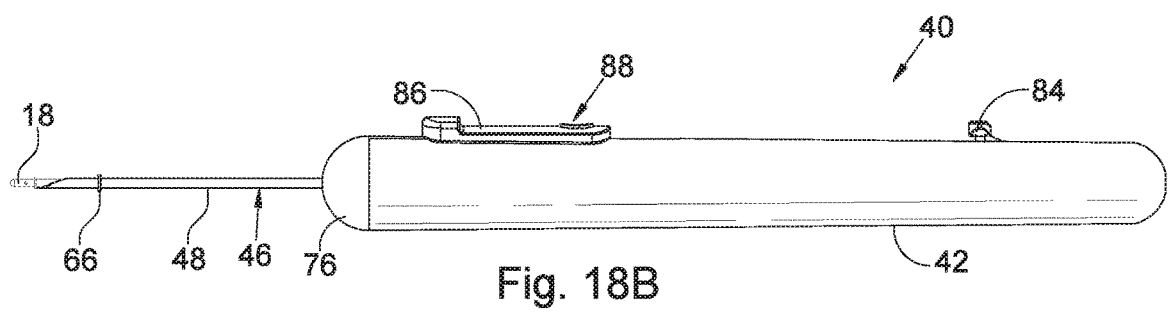
Figure 18C:
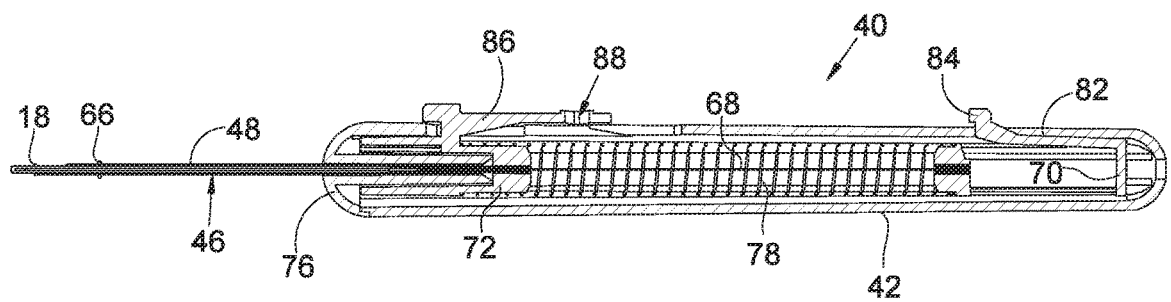

With reference to FIGS. 16 to 18, the shunt is advanced via a manual force applied by a surgeon on the slider block 72. Referring to FIG. 16, the shunt is initially wholly received within the lancet 48. The slider block is in a retracted position with the piston 70 in an extended position in abutment with the slider block. In this position, the stylet is received within the lumen of the distal tube 18. In order to advance the distal tube distally, the slider block 72 is displaced distally by the surgeon as is shown in FIG. 17, causing a distal end 92 of the stylet to exert a force on an inner side of the closed end of the distal tube, advancing the distal tube distally so that a distal end region of the distal tube projects from the lancet.

The distal stop formation 26 of the distal tube 18, being resiliently compressible, is compressed when the distal end of the shunt is received within the lancet. Upon advancement of the distal tube from the lancet, the distal stop formation expands, the outer diameter thereof being relatively larger than the outer diameter of the proximal stop formation 30 in its expanded configuration.

After implantation of the distal tube of the shunt into the subarachnoid space, the lancet of the shunt inserting device is retracted leaving the distal tube in its implanted condition. Referring to FIG. 18, the engagement projection 84 of the piston 70 is pushed inwardly causing the piston to be released from its engagement with the slider block thereby causing displacement, under the action of the coil spring, of the piston into its retraction position and thereby withdrawal of the stylet from the distal tube.

Figure 19A:
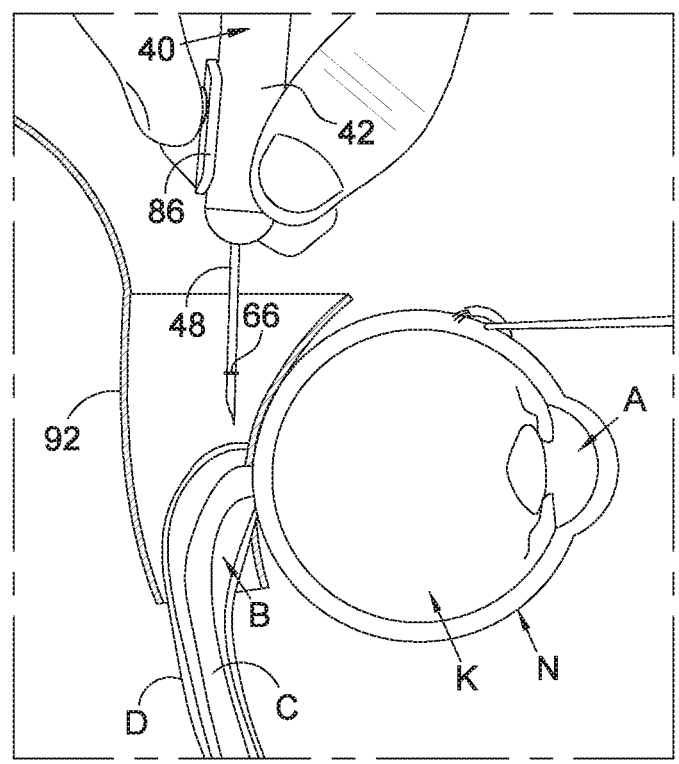
FIGS. 19A-19E show, in sequence, the manner in which the distal end of the shunt is implanted in the subarachnoid space surrounding the optic nerve.
Figure 19B:
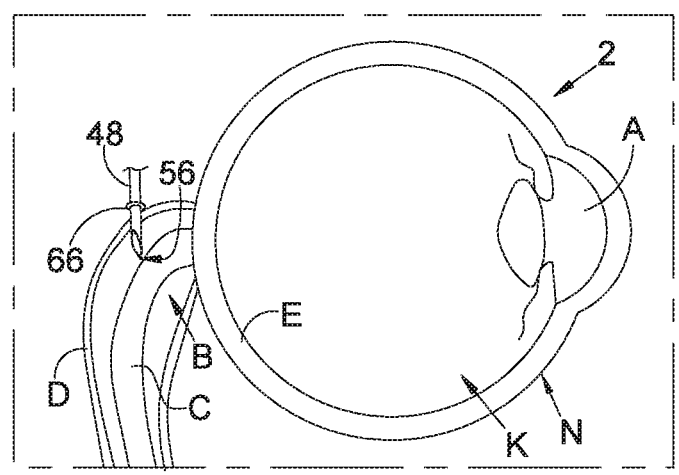
Figure 19C:
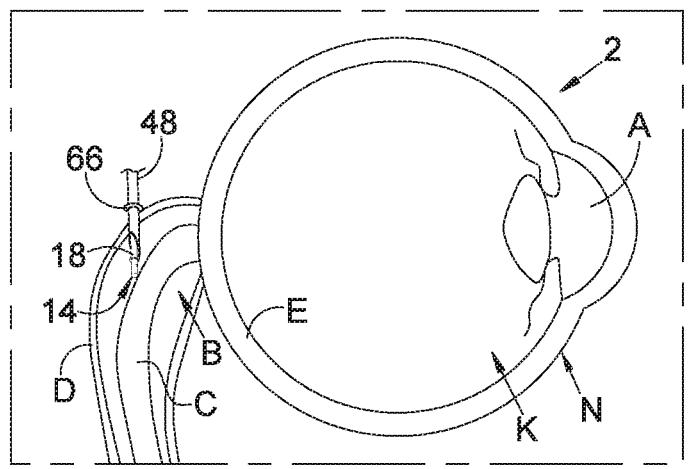
Figure 19D:
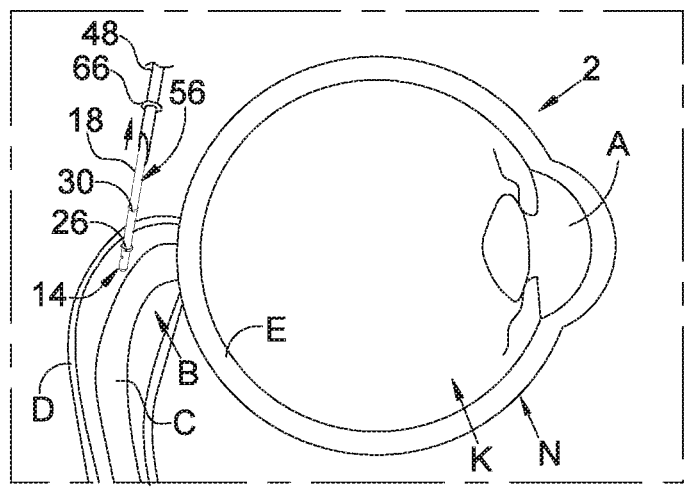
Figure 19E:
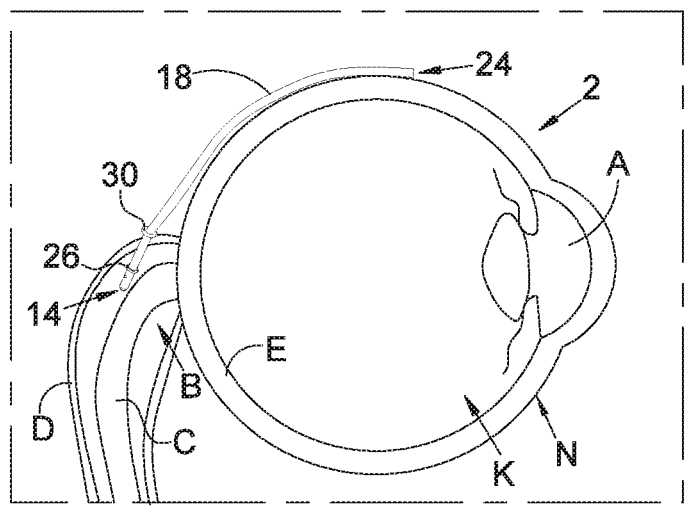

With reference to FIGS. 19A-19E, the manner in which the distal tube 18 of the shunt 10 is implanted in the subarachnoid space, is illustrated, in sequence. A passageway is created through orbital connective tissue surrounding the ocular orbit using an orbital retractor device 92. Once the passageway has been created, the lancet 48 of the shunt inserting device is inserted into the orbital retractor with a clear pathway defined to the optic nerve sheath (FIG. 19A). The tissue-penetrating tip 56 of the lancet is inserted through the optic nerve sheath D into the subarachnoid space B. During insertion, the stop formation 66 of the lancet abuts against an external side of the optic nerve sheath preventing over-insertion of the lancet (FIG. 19B). The slider block is displaced distally by the surgeon causing the distal end of the distal tube 18 of the shunt to be advanced into the subarachnoid space (FIG. 19C). The piston 50 of the shunt inserting device is thereafter disengaged from the slider block 72, causing retraction of the piston and withdrawal of the stylet 68. Upon withdrawal of the stylet, the support sleeve 95 supports the distal tube at its end 24 so as to prevent withdrawal of the distal tube along with the stylet. The shunt inserting device is then removed via the orbital retractor leaving the distal end of the distal tube implanted in the subarachnoid space with the remainder of the distal tube extending along a side of the orbital globe.

Figure 20A:
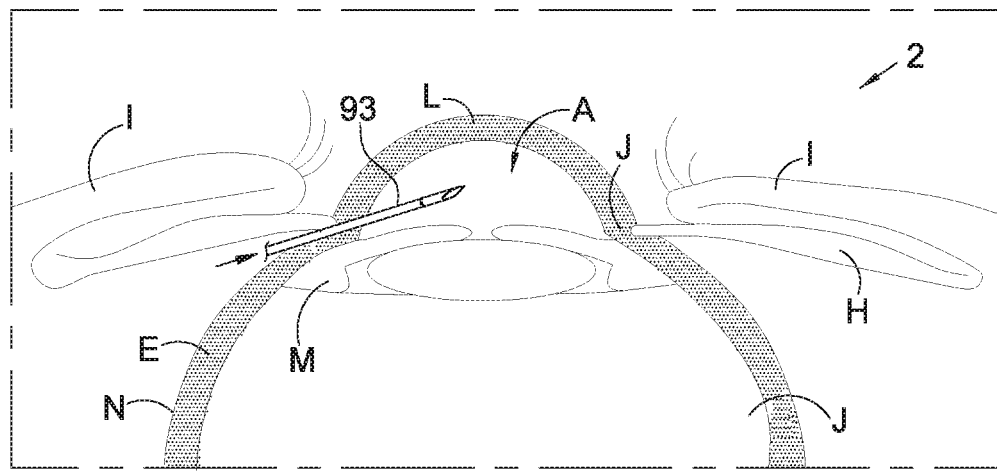
FIGS. 20A-20C show, in sequence, the manner in which the proximal end of the shunt is implanted in the anterior chamber of the eye.
Figure 20B:
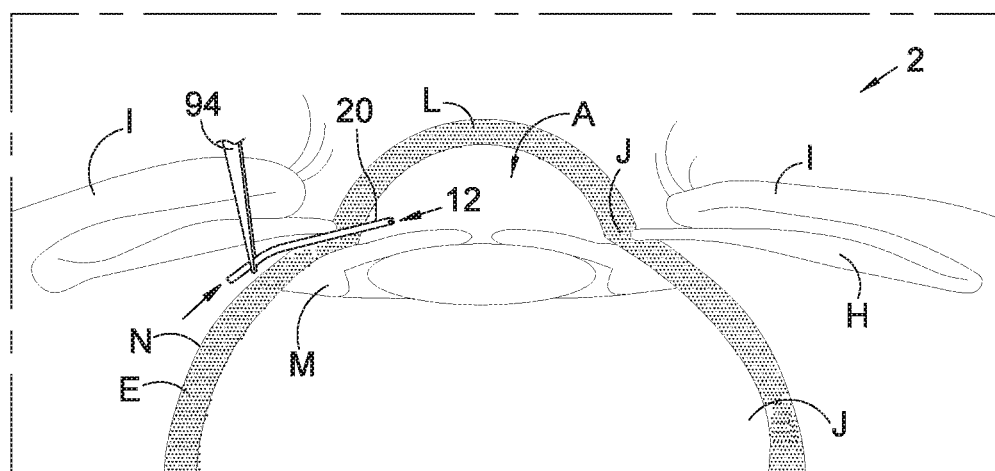
Figure 20C:
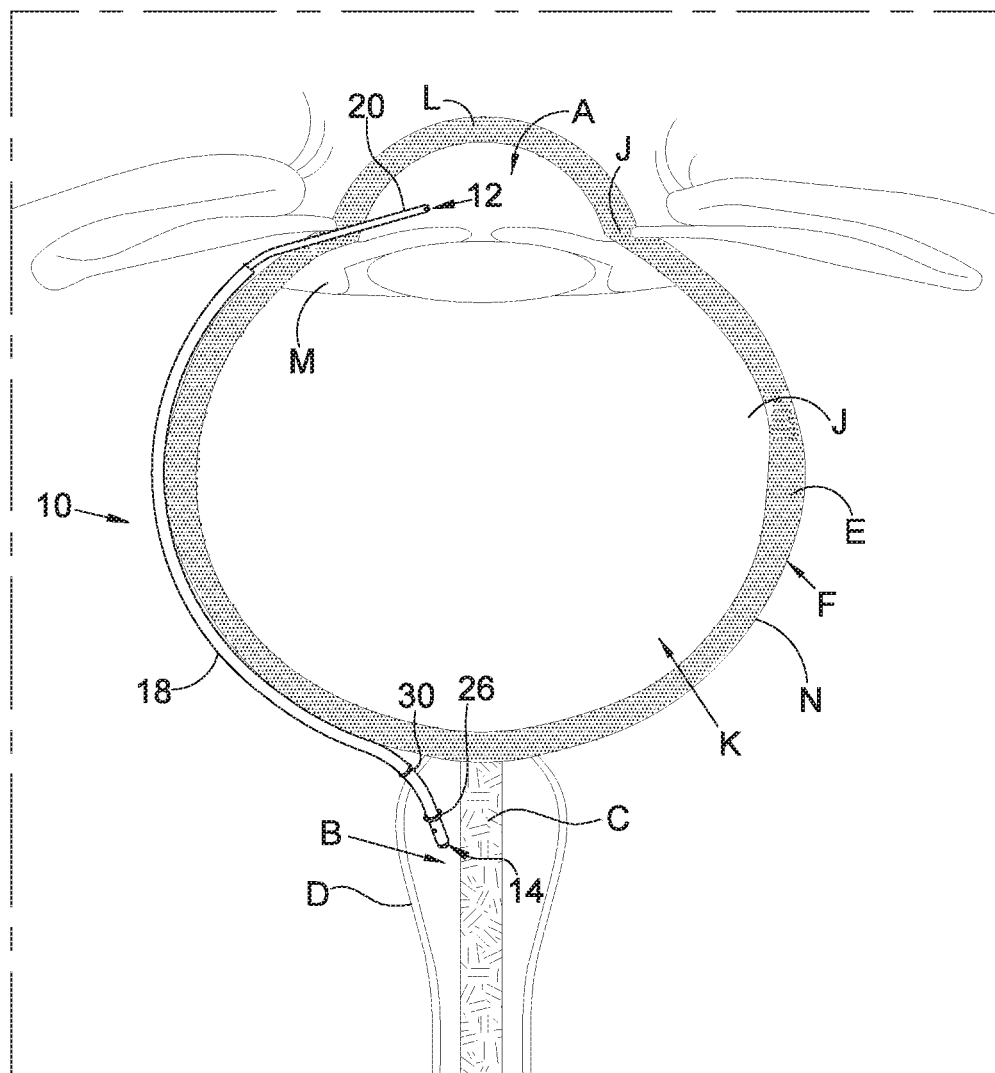
Figure 21:
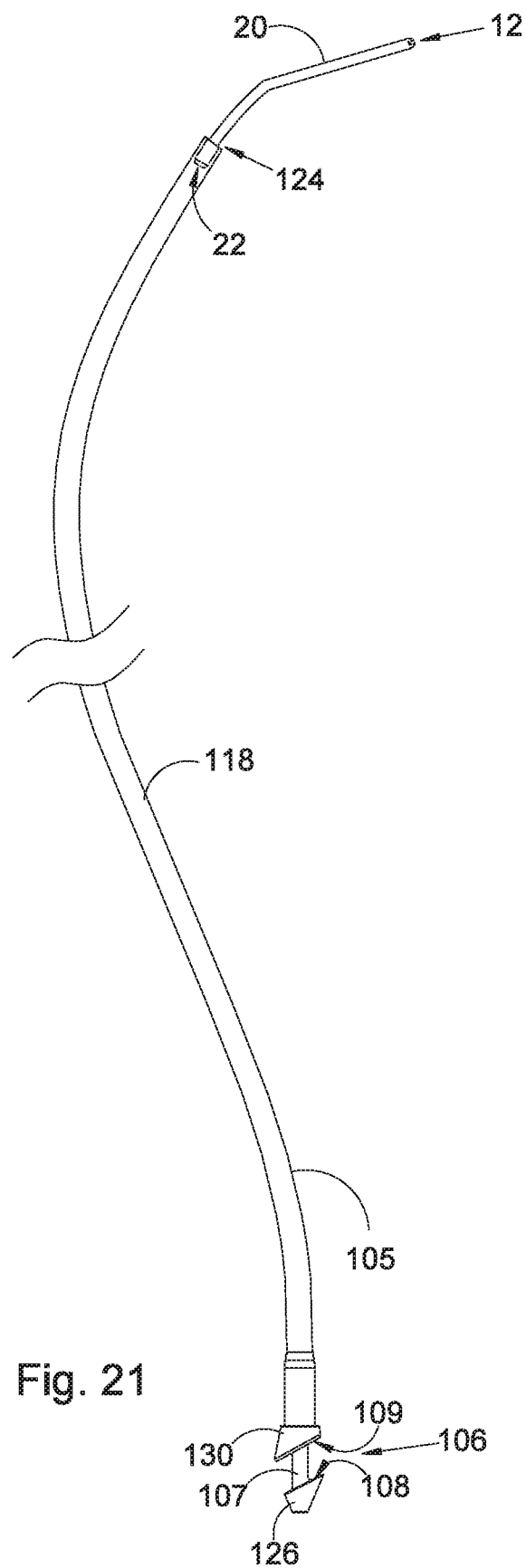
FIG. 21 shows a side view of a second embodiment of a shunt in accordance with the invention.
Figure 22:
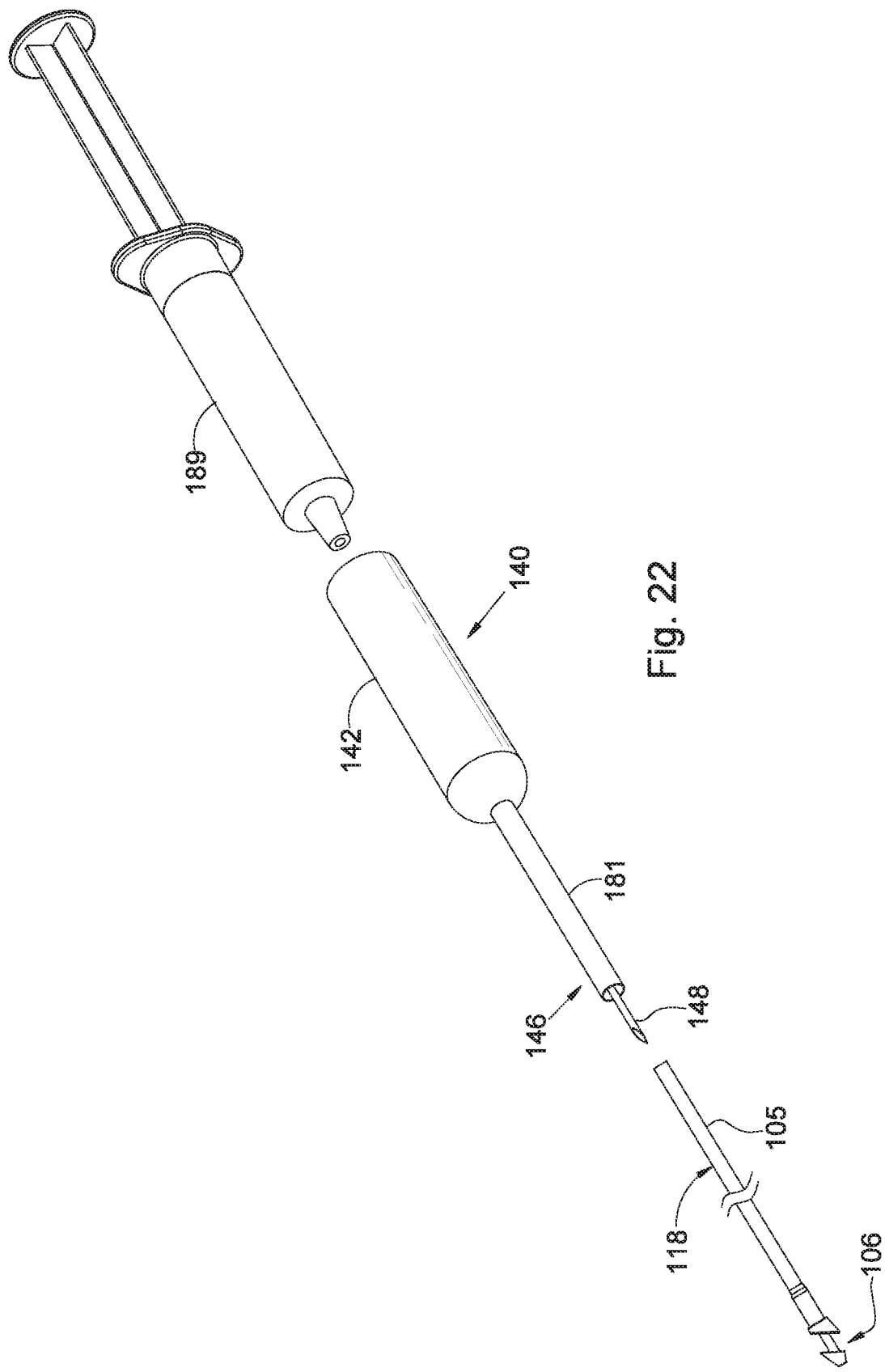
FIG. 22 shows an exploded three-dimensional view of a distal tube of the shunt of FIG. 21 and a shunt inserting device for implanting the distal tube in the subarachnoid space.
Figure 23:
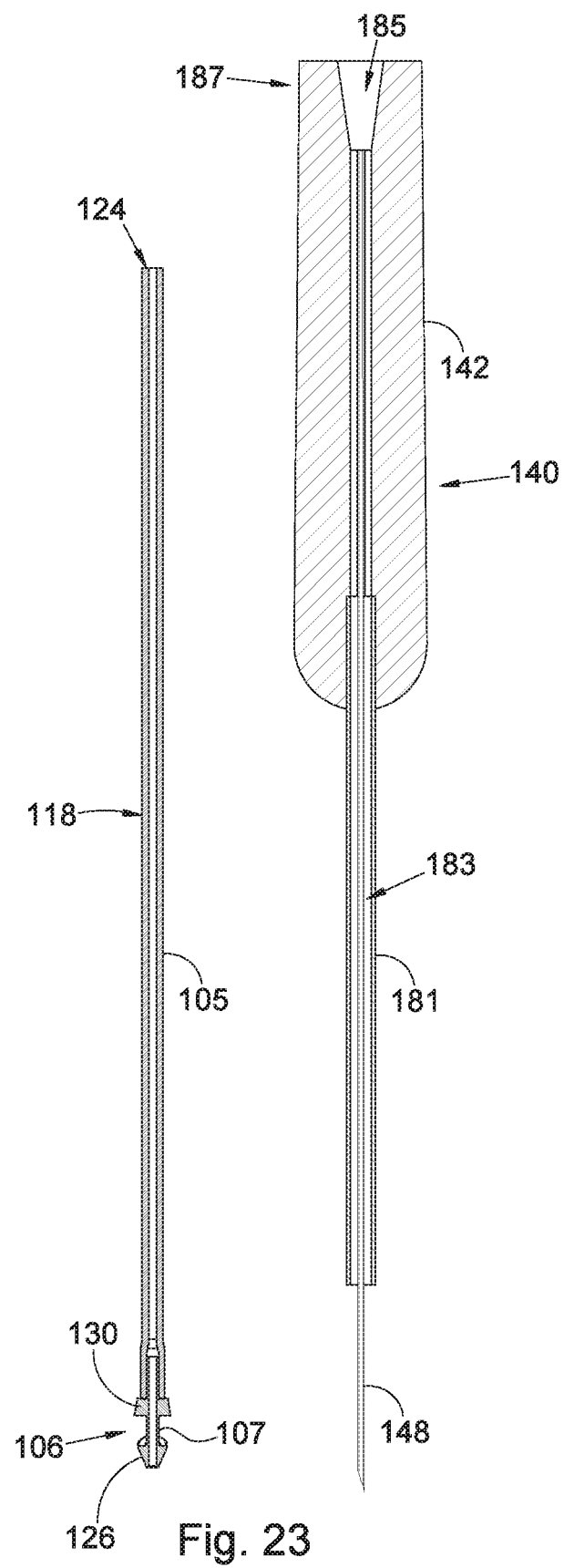
FIG. 23 shows an exploded sectional side view of the distal tube and shunt inserting device of FIG. 22.

With reference to FIGS. 20A-20C, the proximal end of the proximal tube is implanted in the anterior chamber of the ocular globe, by initially creating a scleral channel through the sclera using a surgical blade 93 which enters the sclera about 4 mm from the limbus and exits the sclera at the trabecular meshwork (FIG. 20). Thereafter, the straight section 34 of the rigid proximal tube 20 is advanced along the scleral channel using forceps 94 (FIG. 20B). After implantation of the proximal end 12 in the anterior chamber the opposite end 22 of the proximal tube is inserted into the end 20 of the distal tube thereby forming the shunt between the anterior chamber and the subarachnoid space (FIG. 20C).

With reference to FIGS. 21 to 30, a second embodiment of a shunt in accordance with the invention, is designated by the reference numeral 100. The shunt 100 is similar to the shunt 10 with the only difference being that the distal tube has a different configuration at the distal end thereof. The proximal tube of the shunt 100 is the same as the proximal tube 20 of the shunt 10. In FIGS. 21 to 30, those features of the shunt 100 which are the same as and/or similar to those of the shunt 10 are designated by the same and/or similar reference numerals.

The shunt 100 comprises the rigid proximal tube 20 and a flexible distal tube 118 to which the proximal tube 20 is releasably connected. The distal tube 118 comprises an elongate flexible tubular body 105 of silicone rubber and a rigid implant body 106 of titanium, PEEK or other suitable material.

The rigid implant body 106 of the distal tube 118 defines a distal end 114 of the shunt 100. The distal tube 118 is connected to the proximal tube 20 at an opposite end 24 of the distal tube 118. More specifically, the end 22 of the proximal tube 20 is press-fitted into the open end 24 of the distal tube.

The distal tube 118 and the proximal tube 20 of the shunt 100, define a lumen 116 which extends continuously through the shunt between the distal end 114 and the proximal end 12 thereof.

The implant body 106 comprises a distal stop formation 126, a proximal stop formation 130 which is spaced from the distal stop formation and a narrower neck 107 which extends between the stop formations. The distal stop formation and the proximal stop formation define inwardly facing abutment faces 108 and 109, respectively, which abut inner and outer sides, respectively, of the optic nerve sheath when the distal stop formation 126 is implanted in the subarachnoid space as will be explained in more detail hereinbelow. A distal end region of the implant body is tapered towards the distal end 114 for facilitating advancement of the distal stop formation through a passageway created in the optic nerve sheath.

The abutment faces 108, 109, are disposed opposite one another and are obliquely slanted so as to conform to the curvature of inner and outer surfaces of the optic nerve sheath following implantation.

The invention extends to a shunt system including the shunt 100 and a shunt inserting device 140 for implanting the distal tube 118 in the subarachnoid space.

The shunt inserting device 140 comprises a tubular housing 142 and a distal inserting portion 146 mounted to the housing. The tubular housing provides a handle by which the shunt inserting device can be held.

The distal inserting portion includes an inner lancet 148 defining an internal passageway 150. The lancet has a distal end 152 which is identical to the distal end 52 of the shunt inserting device 40. As such, the lancet defines a tissue-penetrating tip 156 at the distal end for penetrating the optic nerve sheath for defining a passage therethrough through which the distal end of the implant body 106 can pass. The distal inserting portion further includes a tubular outer sleeve 181 within which the lancet is located in a spaced arrangement wherein the lancet and the outer sleeve are co-axially arranged and define an annular space 183 within which the tubular body 105 of the distal tube 118 is displaceably received.

The lancet 148 extends into the housing to a location at a proximal end region of the housing. The housing defines an inlet port 185 at a proximal end 187 thereof which is in fluid flow communication with the passageway 150 of the lancet, to which an outlet of a syringe 189 or the like, containing a gas or a liquid, can be connected.

Figure 28A:
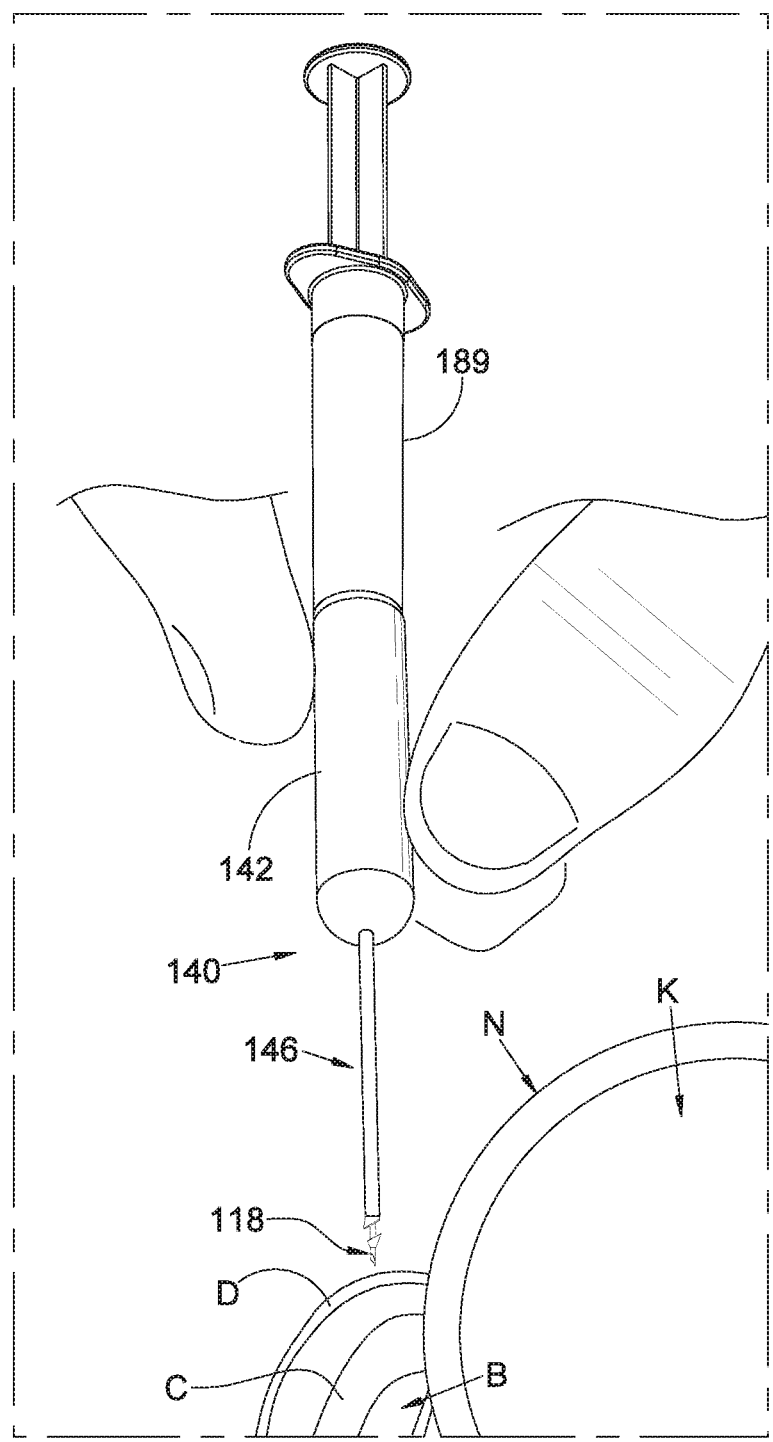
FIGS. 28A-28E show, in sequence, the manner in which the distal end of the second embodiment of the shunt is implanted in the subarachnoid space surrounding the optic nerve.
Figure 28B:
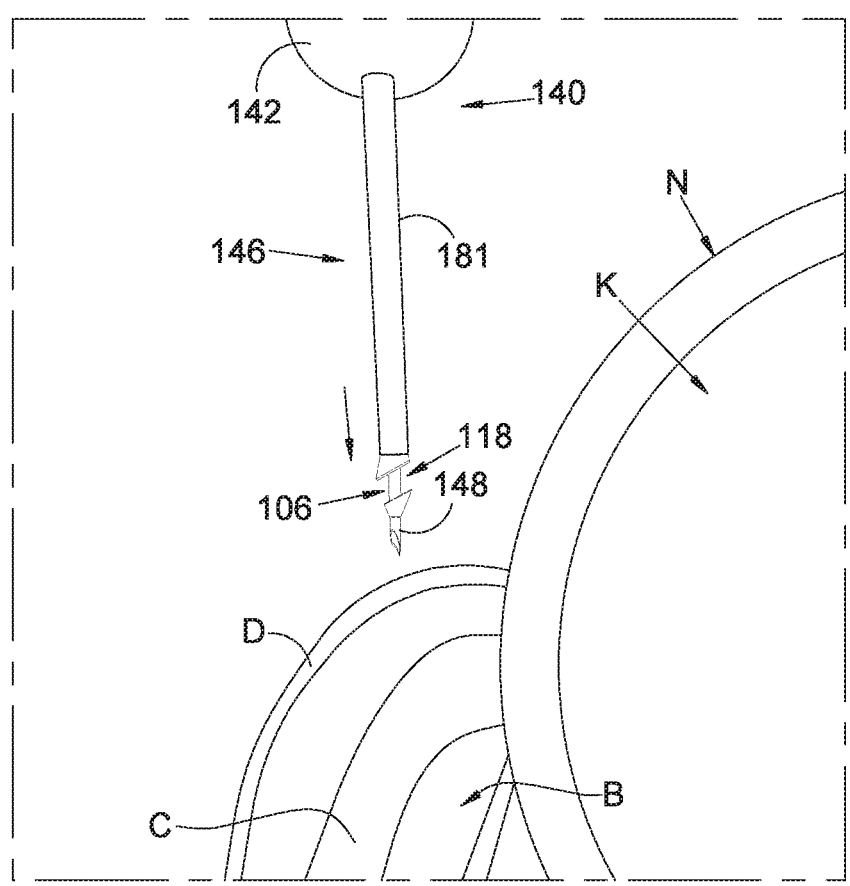
Figure 28C:
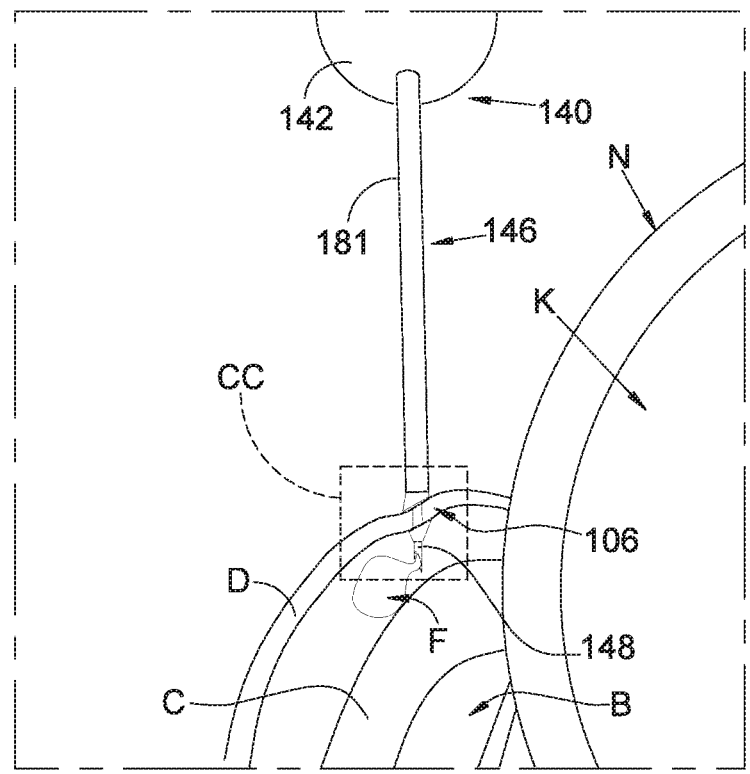
Figure 28C:
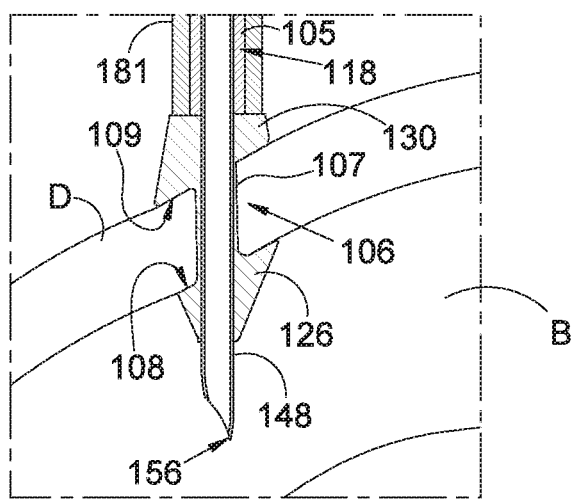
Figure 28D:
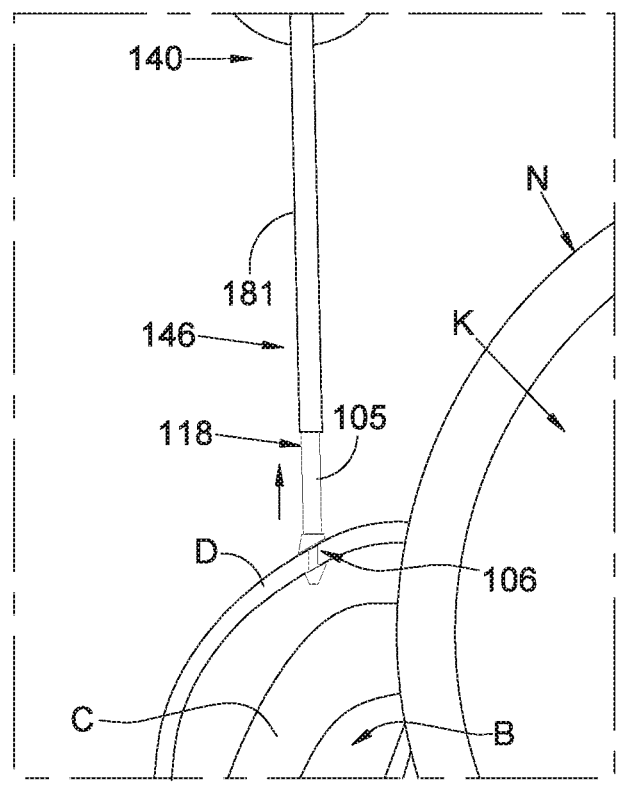
Figure 28E:
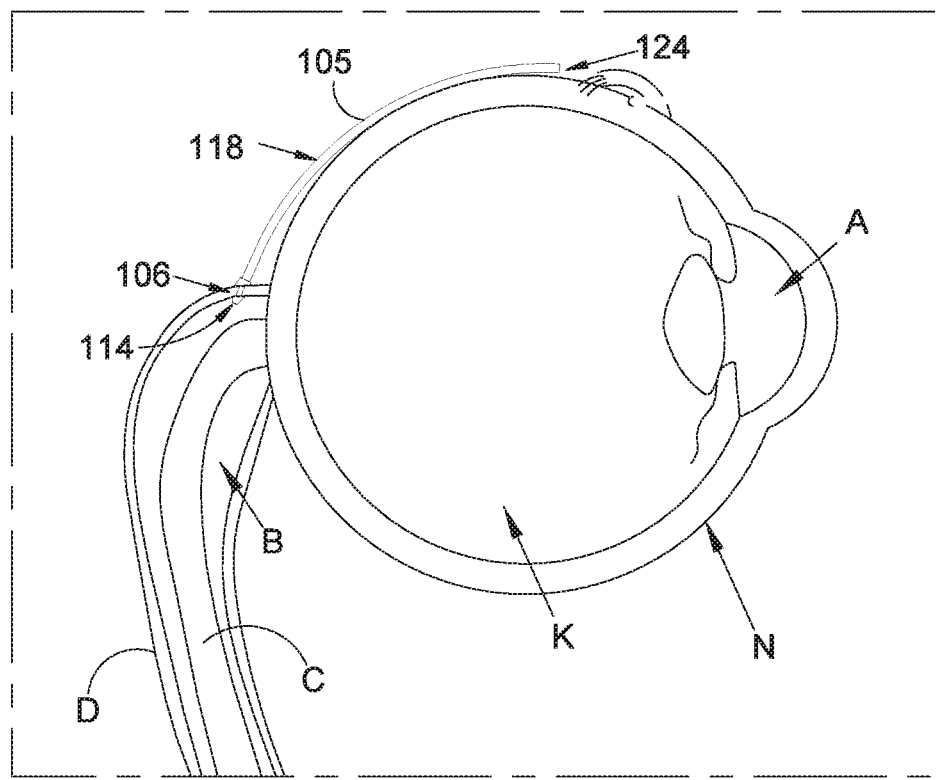

With reference to FIGS. 28A-28E, the manner in which the distal tube 118 of the shunt 100 is implanted in the subarachnoid space, is illustrated, in sequence. A passageway is created through orbital connective tissue surrounding the ocular orbit using an orbital retractor device. Once the passageway has been created, the shunt inserting device 140 having the syringe 189 containing a biocompatible gas or liquid F connected thereto, is inserted (FIGS. 28A-28B) into the orbital retractor (not shown). The gas or liquid is introduced into the subarachnoid space via the lancet 148 by the surgeon by depressing the piston of the syringe thereby to displace the optic nerve sheath and the optic nerve away from one another so as to avoid the tissue-penetrating tip 156 of the lancet 148 accidentally piercing the optic nerve. The tissue penetrating tip 156 of the lancet is inserted through the optic nerve sheath D into the subarachnoid space B (FIGS. 28C-28CC). The shunt inserting device 140 is advanced distally until the distal stop formation 126 of the implant body 106 passes through the aperture defined in the optic nerve sheath by the tissue-penetrating tip 156 of the lancet 148 and the neck 107 of the implant body is located in the aperture in the optic nerve sheath. The implant body is now securely located within the optic nerve sheath with the opposing abutment faces 108 and 109 of the distal stop formation 126 and the proximal stop formation 130, respectively, abutting internal and external sides, respectively, of the optic nerve sheath. Thereafter the shunt inserting device 140 is withdrawn (FIG. 28D) leaving behind the distal tube 118 having its distal end 114 implanted in the subarachnoid space (FIG. 28E).

The invention claimed is:

1. A shunt for treating an ocular disorder related to a disorder of intraocular or intracranial pressure by regulating intraocular pressure in an eye of a patient, the shunt comprising: a proximal shunt portion defining a proximal end which is implantable in an ocular anterior chamber of the patient and a distal shunt portion defining a distal end which is implantable in a subarachnoid space of the patient, the shunt defining a lumen extending longitudinally between the distal and proximal ends, the shunt having an enlarged distal stop formation near the distal end of the shunt, configured to be disposed in the subarachnoid space after implantation of a distal end region of the shunt in the subarachnoid space, for resisting withdrawal of the shunt after implantation in the subarachnoid space, and the shunt being flexible along a portion of a length of the shunt configured to conform to an outer anatomical curvature of an ocular globe, the proximal shunt portion including at least one outwardly-projecting ridge formation for resisting migration of the proximal shunt portion after implantation thereof in the ocular anterior chamber, the distal shunt portion and the proximal shunt portion being releasably connected to one another at a connection point with the lumen of the shunt extending continuously through the distal and proximal shunt portions, the proximal shunt portion having a rigid construction at the connection point which is configured to be along an outer surface of the ocular globe, wherein a portion of the proximal shunt portion is releasably received within the distal shunt portion.

2. The shunt as claimed in claim 1, wherein the shunt has an enlarged proximal stop formation near the distal end of the shunt disposed at a position spaced from the distal stop formation at a location relatively closer to the proximal end of the shunt, the proximal stop formation configured to be disposed externally of the optic nerve sheath upon implantation of the distal end of the shunt in the subarachnoid space, thereby preventing over-migration of the shunt into the subarachnoid space.

3. The shunt as claimed in claim 1, wherein the distal shunt portion comprises an elongate flexible tubular body and a rigid implant body connected to a distal end of the flexible tubular body, which defines the distal end of the shunt, the proximal shunt portion facilitating advancement of the proximal shunt portion along a scleral passageway defined in the sclera extending to the ocular anterior chamber.

4. The shunt as claimed in claim 1, wherein the distal end of the shunt has a tapered end region tapering towards the distal end of the shunt, for facilitating advancement of the distal end region of the shunt along an anatomical passageway.

5. The shunt as claimed in claim 1, wherein a proximal end region of the proximal shunt portion tapers towards the proximal end of the shunt, thereby facilitating displacement of the proximal shunt portion along a scleral passageway.

6. The shunt as claimed in claim 1, wherein a wall of the proximal shunt portion has two or more slots thereby permitting drainage of aqueous fluid into the lumen of the shunt from different directions.

7. The shunt as claimed in claim 1, wherein the proximal shunt portion has a straight section at a proximal end region of the shunt terminating in the proximal end of the shunt, permitting the straight section to be displaced along a scleral passageway defined in the sclera extending to the ocular anterior chamber and further comprises a curved section spaced from the proximal end of the shunt, the curved section having a curvature which conforms to an anatomical curvature of the ocular globe.

8. The shunt as claimed in claim 1, wherein the proximal shunt portion includes an outwardly-projecting locating formation for engagement by a suture for suturing the proximal shunt portion to the sclera to hold the proximal shunt portion in place.

9. The shunt as claimed in claim 1, wherein the distal stop formation is deformable.

10. The shunt as claimed in claim 9, wherein the distal stop formation is resiliently compressible.

11. The shunt as claimed in claim 1, wherein a distal end of the shunt is closed, with one or more fluid flow openings leading into the lumen being defined in a side wall of the shunt near the distal end thereof.

12. The shunt as claimed in claim 1, wherein the shunt incorporates an elutable therapeutic substance.

13. The shunt as claimed in claim 12, wherein the elutable therapeutic substance is selected from a group consisting of an antibiotic, an anticlotting agent, and an anti-vascular endothelial growth factor.

14. The shunt as claimed in claim 1, further comprising a shunt inserting device including:
   a) a distal insertion portion for displaceably supporting the shunt, the distal insertion portion defining a tissue-penetrating tip for penetrating the optic nerve sheath configured to form a passage in the optic nerve sheath surrounding the subarachnoid space; and
   b) a shunt advancing device for displacing the shunt through the passage in the optic nerve sheath for implanting the distal end of the shunt in the subarachnoid space.

15. The shunt system as claimed in claim 14, wherein the distal insertion portion of the shunt inserting device comprises an elongate hollow shaft defining an internal passageway within which the shunt is slidably received and displaceable.

16. The shunt system as claimed in claim 15, wherein the distal end of the shunt is closed, the shunt advancing device including an elongate advancing element having a proximal end and a distal end, the distal end of the advancing element being located slidably within the hollow shaft for abutment with an inner side of the closed distal end of the shunt for exerting a force on the distal end of the shunt for advancing the shunt, the shunt defining at least one fluid flow opening near the distal end extending into the lumen of the shunt for permitting fluid to pass therethrough.

17. The shunt system as claimed in claim 15, wherein the distal insertion portion comprises a lancet having a taper cut defining the tissue-penetrating tip of the distal insertion portion, the taper cut having a distal end and a proximal end, and wherein a distal end region of the taper cut is sharp-edged while a proximal end region of the taper cut has blunt edges.

18. The shunt system as claimed in claim 14, wherein the shunt has a flexible distal end region and wherein the distal stop formation is resiliently compressible, the distal stop formation being locatable within the subarachnoid space upon implantation of the distal end therein and compressible when received within the distal insertion portion of the shunt inserting device and expandable after discharge from the distal insertion portion.

19. The shunt system as claimed in claim 15, wherein the distal insertion portion has an outwardly-projecting stop formation spaced from the tissue-penetrating tip for preventing over-insertion of the distal insertion portion into the subarachnoid space.

20. The shunt system as claimed in claim 14, wherein the distal insertion portion comprises the lancet and a tubular outer support member which is co-axially disposed relative to the lancet and spaced therefrom to thereby define an annular space between the lancet and the outer support member within which the shunt is slidably received and displaceable.

21. The shunt system as claimed in claim 16, wherein the advancing element is releasably connected to the actuator of the slider when advancing the advancing element within the hollow shaft.

22. The shunt system as claimed in claim 16, which includes a coil spring which acts between the slider and the advancing element for urging the advancing element in a proximal direction away from the slider upon release of the slider.

23. The shunt system as claimed in claim 20, wherein the lancet defines an internal passage therethrough.

24. The shunt system as claimed in claim 23, which includes a housing to which the lancet is mounted, the housing including an inlet port which is in flow communication with the passage of the lancet and to which an outlet of a mechanism for displacing a gas or a liquid along the passage of the lancet can be connected.

25. A shunt for treating an ocular disorder related to a disorder of intraocular or intracranial pressure by regulating intraocular pressure in an eye of a patient, the shunt comprising: a proximal shunt portion defining a proximal end which is implantable in an ocular anterior chamber of the patient and a distal shunt portion defining a distal end which is implantable in a subarachnoid space of the patient, the shunt defining a lumen extending longitudinally between the distal and proximal ends, the shunt having an enlarged distal stop formation near the distal end of the shunt, configured to be disposed in the subarachnoid space after implantation of a distal end region of the shunt in the subarachnoid space, for resisting withdrawal of the shunt after implantation in the subarachnoid space, and the shunt being flexible along a portion of a length of the shunt configured to conform to an outer anatomical curvature of an ocular globe, the proximal shunt portion including at least one outwardly-projecting ridge formation for resisting migration of the proximal shunt portion after implantation thereof in the ocular anterior chamber, the distal and proximal shunt portions being releasably connected at a connection point located along an outer surface of the ocular globe, with the lumen of the shunt extending continuously through the distal and proximal shunt portions, the proximal shunt portion having a rigid construction at the connection point which is configured to be along the outer surface of the ocular globe, wherein a portion of the proximal shunt portion is releasably received within the distal shunt portion.

26. A shunt for treating an ocular disorder related to a disorder of intraocular or intracranial pressure by regulating intraocular pressure in an eye of a patient, the shunt comprising: a proximal shunt portion defining a proximal end which is implantable in an ocular anterior chamber of the patient and a distal shunt portion defining a distal end which is implantable in a subarachnoid space of the patient, the shunt defining a lumen extending longitudinally between the distal and proximal ends, the shunt having an enlarged distal stop formation near the distal end of the shunt, configured to be disposed in the subarachnoid space after implantation of a distal end region of the shunt in the subarachnoid space, for resisting withdrawal of the shunt after implantation in the subarachnoid space, and the shunt being flexible along a portion of a length of the shunt configured to conform to an outer anatomical curvature of an ocular globe, the proximal shunt portion including at least one outwardly-projecting ridge formation for resisting migration of the proximal shunt portion after implantation thereof in the ocular anterior chamber, the distal and proximal shunt portions being releasably connected in a press-f it at a connection point, with the lumen of the shunt extending continuously through the distal and proximal shunt portions, the proximal shunt portion having a rigid construction at the connection point which is configured to be along an outer surface of the ocular globe, wherein a portion of the proximal shunt portion is releasably received within the distal shunt portion.

* * * * *